(12) United States Patent
Clark

(10) Patent No.: US 9,095,275 B2
(45) Date of Patent: Aug. 4, 2015

(54) CONTACT SENSORS AND METHODS FOR MAKING SAME

(76) Inventor: Andrew C. Clark, Greenville, SC (US)

( * ) Notice: Subject to any disclaimer, the term of this patent is extended or adjusted under 35 U.S.C. 154(b) by 701 days.

(21) Appl. No.: 13/376,037

(22) PCT Filed: Jun. 3, 2010

(86) PCT No.: PCT/US2010/037285
§ 371 (c)(1),
(2), (4) Date: Jan. 30, 2012

(87) PCT Pub. No.: WO2010/141742
PCT Pub. Date: Dec. 9, 2010

(65) Prior Publication Data
US 2012/0123716 A1    May 17, 2012

Related U.S. Application Data

(60) Provisional application No. 61/183,843, filed on Jun. 3, 2009.

(51) Int. Cl.
| | |
|---|---|
| *G01L 1/00* | (2006.01) |
| *A61F 2/38* | (2006.01) |
| *A61B 5/07* | (2006.01) |
| *G01L 1/20* | (2006.01) |
| *A61B 5/00* | (2006.01) |
| *A61B 5/107* | (2006.01) |

(52) U.S. Cl.
CPC ............... *A61B 5/076* (2013.01); *A61B 5/0031* (2013.01); *A61B 5/6846* (2013.01); *G01L 1/205* (2013.01); *A61B 5/107* (2013.01); *A61B 5/4528* (2013.01); *A61B 5/4533* (2013.01); *A61B 2562/0247* (2013.01); *A61B 2562/046* (2013.01)

(58) Field of Classification Search
CPC ...... A61B 5/076; A61B 5/6846; A61B 5/107; A61B 5/4528; A61B 2562/0247; G01L 1/205
USPC .............. 73/862.68, 172, 768, 760, 763, 777, 73/719, 774, 818, 862.041–862.046, 73/862.474; 623/20.14; 600/547
See application file for complete search history.

(56) References Cited

U.S. PATENT DOCUMENTS

| | | | | | |
|---|---|---|---|---|---|
| 4,145,317 | A | * | 3/1979 | Sado et al. | 252/512 |
| 4,273,682 | A | * | 6/1981 | Kanamori | 252/511 |
| 4,302,361 | A | * | 11/1981 | Kotani et al. | 252/503 |
| 4,314,227 | A | * | 2/1982 | Eventoff | 338/99 |
| 4,394,773 | A | * | 7/1983 | Ruell | 382/124 |
| 4,489,302 | A | * | 12/1984 | Eventoff | 338/99 |
| 4,492,949 | A | * | 1/1985 | Peterson et al. | 338/114 |
| 4,495,236 | A | * | 1/1985 | Obara et al. | 428/172 |

(Continued)

*Primary Examiner* — Lisa Caputo
*Assistant Examiner* — Jonathan Dunlap
(74) *Attorney, Agent, or Firm* — Ballard Spahr LLP

(57) ABSTRACT

Disclosed herein are novel contact sensors. The contact sensors disclosed herein include a conductive composite material formed of a polymer and a conductive filler. In one particular aspect, the composite materials can include less than about 10 wt % conductive filler. Thus, the composite material of the contact sensors can have physical characteristics essentially identical to the polymer, while being electrically conductive with the electrical resistance proportional to the load on the sensor. The sensors can provide real time dynamic contact information for joint members under conditions expected during use. In one particular aspect, the sensor can be used to properly balance the knee ligaments in a total knee replacement surgery.

21 Claims, 19 Drawing Sheets

(56) References Cited

U.S. PATENT DOCUMENTS

| | | | |
|---|---|---|---|
| 4,553,837 A * | 11/1985 | Marcus | 356/71 |
| 4,634,623 A * | 1/1987 | Watkins | 428/208 |
| 4,734,034 A * | 3/1988 | Maness et al. | 433/68 |
| 4,856,993 A * | 8/1989 | Maness et al. | 433/68 |
| 5,033,291 A * | 7/1991 | Podoloff et al. | 73/172 |
| 5,042,504 A * | 8/1991 | Huberti | 600/592 |
| 5,060,527 A * | 10/1991 | Burgess | 73/862.68 |
| 5,083,573 A * | 1/1992 | Arms | 600/587 |
| 5,113,512 A * | 5/1992 | Miki et al. | 711/206 |
| 5,197,488 A * | 3/1993 | Kovacevic | 600/595 |
| 5,278,703 A * | 1/1994 | Rub et al. | 360/51 |
| 5,302,936 A * | 4/1994 | Yaniger | 338/47 |
| 5,360,016 A * | 11/1994 | Kovacevic | 600/595 |
| 5,422,061 A * | 6/1995 | Takahashi et al. | 264/571 |
| 5,470,354 A * | 11/1995 | Hershberger et al. | 128/898 |
| 5,541,570 A * | 7/1996 | McDowell | 338/47 |
| 5,583,630 A * | 12/1996 | Kimura et al. | 399/227 |
| 5,603,002 A | 2/1997 | Hashimoto | 711/113 |
| 5,719,098 A * | 2/1998 | Hahn et al. | 502/407 |
| 5,756,904 A * | 5/1998 | Oreper et al. | 73/862.046 |
| 5,818,956 A * | 10/1998 | Tuli | 382/126 |
| 5,880,976 A * | 3/1999 | DiGioia, III et al. | 703/7 |
| 5,887,199 A * | 3/1999 | Ofer et al. | 710/65 |
| 5,989,700 A * | 11/1999 | Krivopal | 428/323 |
| 5,993,400 A * | 11/1999 | Rincoe et al. | 600/595 |
| 5,997,829 A * | 12/1999 | Sekine et al. | 423/210 |
| 6,032,542 A * | 3/2000 | Warnick et al. | 73/862.627 |
| 6,073,497 A * | 6/2000 | Jiang et al. | 73/862.68 |
| 6,136,412 A * | 10/2000 | Spiewak et al. | 428/143 |
| 6,155,120 A * | 12/2000 | Taylor | 73/862.046 |
| 6,207,775 B1 * | 3/2001 | Marti et al. | 526/160 |
| 6,216,545 B1 * | 4/2001 | Taylor | 73/862.046 |
| 6,267,011 B1 * | 7/2001 | Kurtz et al. | 73/789 |
| 6,273,863 B1 * | 8/2001 | Avni et al. | 600/587 |
| 6,283,829 B1 * | 9/2001 | Molnar | 451/8 |
| 6,319,293 B1 * | 11/2001 | Debe et al. | 29/623.3 |
| 6,363,796 B1 * | 4/2002 | Jiang et al. | 73/862.046 |
| 6,441,084 B1 * | 8/2002 | Lee et al. | 524/495 |
| 6,447,448 B1 * | 9/2002 | Ishikawa et al. | 600/300 |
| 6,520,030 B1 * | 2/2003 | Jiang et al. | 73/862.06 |
| 6,524,742 B1 * | 2/2003 | Emanuel et al. | 429/129 |
| 6,539,815 B1 * | 4/2003 | Jiang et al. | 73/862.06 |
| 6,543,299 B2 * | 4/2003 | Taylor | 73/862.046 |
| 6,561,044 B1 * | 5/2003 | Jiang et al. | 73/862.06 |
| 6,668,304 B1 * | 12/2003 | Satran et al. | 711/112 |
| 6,684,717 B2 * | 2/2004 | Jiang et al. | 73/862.046 |
| 6,693,441 B2 * | 2/2004 | Lane et al. | 324/662 |
| 6,769,313 B2 * | 8/2004 | Weiss | 73/862.046 |
| 6,820,502 B2 * | 11/2004 | Jiang et al. | 73/862.06 |
| 6,877,385 B2 * | 4/2005 | Fang et al. | 73/777 |
| 6,993,400 B2 * | 1/2006 | Viassolo | 700/99 |
| 7,039,758 B2 * | 5/2006 | Mannen et al. | 711/114 |
| 7,080,562 B2 * | 7/2006 | Knowles et al. | 73/818 |
| 7,097,662 B2 * | 8/2006 | Evans et al. | 623/18.11 |
| 7,128,736 B1 * | 10/2006 | Abrams et al. | 606/1 |
| 7,162,322 B2 * | 1/2007 | Arbogast et al. | 700/118 |
| 7,258,026 B2 * | 8/2007 | Papakostas et al. | 73/862.046 |
| 7,311,009 B2 * | 12/2007 | Kotovsky | 73/777 |
| 7,316,167 B2 * | 1/2008 | DeConde et al. | 73/862.042 |
| 7,377,944 B2 * | 5/2008 | Janusson et al. | 623/36 |
| 7,406,386 B2 * | 7/2008 | Brett et al. | 702/41 |
| 7,430,925 B2 * | 10/2008 | Son et al. | 73/862.046 |
| 7,437,953 B2 * | 10/2008 | DeConde et al. | 73/862.042 |
| 7,470,288 B2 * | 12/2008 | Dietz et al. | 623/20.14 |
| 7,770,473 B2 * | 8/2010 | Von Lilienfeld-Toal et al. | 73/862.68 |
| 7,849,751 B2 * | 12/2010 | Clark et al. | 73/768 |
| 7,926,365 B2 * | 4/2011 | Yeh et al. | 73/862.046 |
| 8,234,929 B2 * | 8/2012 | Clark et al. | 73/776 |
| 8,820,173 B2 * | 9/2014 | Clark et al. | 73/768 |
| 2002/0059276 A1 * | 5/2002 | Wei Loon et al. | 707/100 |
| 2003/0069644 A1 * | 4/2003 | Kovacevic et al. | 623/20.32 |
| 2004/0019382 A1 * | 1/2004 | Amirouche et al. | 623/18.11 |
| 2004/0019384 A1 * | 1/2004 | Kirking et al. | 623/20.14 |
| 2004/0064191 A1 * | 4/2004 | Wasielewski | 623/20.14 |
| 2004/0119701 A1 * | 6/2004 | Mulligan et al. | 345/173 |
| 2005/0177170 A1 * | 8/2005 | Fisher et al. | 606/88 |
| 2005/0241409 A1 * | 11/2005 | Taylor | 73/841 |
| 2005/0273170 A1 * | 12/2005 | Navarro et al. | 623/17.13 |
| 2006/0282006 A1 * | 12/2006 | Petrucelli | 600/547 |
| 2006/0282634 A1 * | 12/2006 | Ohtsuka | 711/167 |
| 2007/0234819 A1 * | 10/2007 | Amirouche et al. | 73/781 |
| 2008/0065225 A1 * | 3/2008 | Wasielewski et al. | 623/18.11 |
| 2010/0130889 A1 * | 5/2010 | Toth et al. | 600/587 |
| 2011/0121840 A1 * | 5/2011 | Sanghera et al. | 324/649 |
| 2012/0118649 A1 * | 5/2012 | Clark et al. | 177/211 |
| 2013/0204157 A1 * | 8/2013 | Clark et al. | 600/547 |

* cited by examiner

CONTACT SENSORS AND METHODS FOR MAKING SAME

CROSS-REFERENCE TO RELATED APPLICATIONS

This application claims the benefit of U.S. Provisional Application No. 61/183,843, filed on Jun. 3, 2009, which application is herein incorporated by reference in its entirety.

BACKGROUND OF THE INVENTION

1. Field of the Invention

This invention relates to contact sensors, and more particularly to contact sensors for accurately measuring surface contact data at a junction between two members.

2. Description of the Related Art

Contact sensors have been used to gather information concerning contact or near-contact between two surfaces in medical applications, such as dentistry, podiatry, and in the development of prostheses, as well as in industrial applications, such as determinations of load and uniformity of pressure between mating surfaces and development of bearings and gaskets. In general, these sensors include pressure-sensitive films designed to be placed between mating surfaces. These film sensors, while generally suitable for examining static contact characteristics between two generally flat surfaces, have presented many difficulties in other situations. For example, when examining contact data between more complex surfaces, including, for example, surfaces with complex curvatures, for example, it can be difficult to conform the films to fit the surfaces without degrading the sensor's performance.

More serious problems exist with these materials as well. For example, film-based contact sensor devices and methods introduce a foreign material having some thickness between the mating surfaces, which can change the contact characteristic of the junction and overestimate the contact areas between the two surfaces. Moreover, the ability to examine real time, dynamic contact characteristics is practically non-existent with these types of sensors.

A better understanding of the contact conditions at joints and junctions could lead to reduced wear in materials, better fit between mating surfaces, and longer life expectancy for machined parts. For example, one of the leading causes of failure in total joint replacement prostheses is loosening of the implant induced by wear debris particles worn from the polymeric bearing component. A better understanding of the contact conditions between the joint components would lead to reduced implant wear and longer implant life.

A leading cause of wear and revision in prosthetics such as knee implants, hip implants and shoulder implants is less than optimum implant alignment. In a Total Knee Arthroplasty (TKA) procedure, for example, current instrument design for resection of bone limits the alignment of the femoral and tibial resections to average values for varus/valgus flexion/extension and external/internal rotation. Additionally, surgeons often use visual landmarks or "rules of thumb" for alignment which can be misleading due to anatomical variability. While the success rate of the TKA procedure has improved tremendously over the past several decades, revision is still required in a significant number of these cases. About 22,000 of these replacements must be revised each year and even more revisions are predicted for other joint revision surgeries.

In a conventional TKA procedure, in order to correctly balance the forces on each side of the implant after the bone resection has been made, the surgeon performs a procedure known as soft tissue balancing, or ligament balancing, where the collateral ligaments of the knee are partially incised to even out the forces. Releasing some of the soft tissue points can change the balance of the knee; however, the multiple options can be confusing for many surgeons. In revision TKA, for example, many of the visual landmarks are no longer present, making alignment and restoration of the joint line difficult. This is one of the most difficult parts of the surgery to reproduce, and currently available products are not sufficient to effectively assist surgeons with this procedure.

These difficulties frequently cause surgeons to unknowingly create TKA misalignment, which is the leading cause of early failure, and which results in pain and suffering for the patient and increases the risks associated with a second surgery to replace the failed joint. Studies have shown that the most sensitive alignment is the varus/valgus tilt of the tibial insert, with an alignment error of as small as 3 degrees being sufficient to cause premature failure of the implant. In a study where the forces on each side of the implant were measured intra-operatively, over 70% were misaligned in the varus/valgus direction.

Accordingly, there is a need in the pertinent art for improved implant selection, positioning, and design, as well as a better understanding of the in vivo forces of the components of the implant as they relate to each other, the bone, and the surrounding soft tissue structures. There is also a need in the pertinent art for improvement in the mechanical and wear characteristics of knee prostheses such that the prostheses may be expected to last a lifetime. There is a further need in the pertinent art for tools with which physicians can perform diagnostics, during surgery, on prostheses implanted within a patient. There is still a further need in the pertinent art for devices, methods and protocols for joint and bone alignment and tracking for preliminary tests during joint replacement surgery.

SUMMARY OF THE INVENTION

In one aspect, the present invention is directed to a contact sensor. The sensor includes an electrically conductive composite material comprising a polymer and a conductive filler. Generally, the composite material can include any polymer. In certain aspects, the polymer can be an engineering polymer or a high performance polymer. In one aspect, the composite material can include ultra-high molecular weight polyethylene (UHMWPE). In another aspect, the composite material can include polyphenylene sulfide (PPS). In one aspect, the composite material of the sensors can include between about 0.1% and 20% by weight of a conductive filler. The conductive filler can be any suitable material. For example, in one aspect, the conductive filler can include carbon black.

The contact sensors of the invention can define a contact surface. In one aspect, a contact surface of the contact sensors of the invention can be placed in a static position so as to replicate a surface that can be placed in proximity to a surface of a second member, thereby forming a junction. In particular, the contact surface of the sensors of the invention can replicate the shape and, optionally, the material characteristics of a junction-forming member found in an industrial, medical, or any other useful setting. For example, in one particular aspect, the contact surface of the sensor can include curvature such as that defined by the contact surface of a polymeric bearing portion of an implantable artificial replacement joint such as the polymeric bearing portion of a hip, knee, or shoulder replacement joint. Alternatively, the contact sensors can be thermoformed into a desired three-dimensional shape. For example, the contact sensors can be thermoformed for use as a prosthetic device.

In one aspect, the sensor can be formed entirely of the composite material. In another aspect, the contact sensors of the invention can include one or more discrete regions of the electrically conductive composite material and a non-conductive material. For example, the sensors can include multiple discrete regions of the electrically conductive composite material that can be separated by an intervening nonconductive material, e.g., an intervening polymeric material. In one particular aspect, the intervening polymeric material separating discrete regions of the composite material can include the same polymer as the polymer of the electrically conductive composite material.

In another aspect, the sensor can comprise one or more sensing points. The sensing points can be configured to measure current flow therethrough the sensing point during application of a load. In one aspect, the current flow measured at each sensing point can be transmitted to a data acquisition terminal. In an additional aspect, the data acquisition terminal can transmit a digital output signal indicative of the current flow measurements to a computer having a processor. In a further aspect, the processor can be configured to calculate the load experienced at each respective sensing point using the digital output signal. In this aspect, the computer can be configured to graphically display the loads experienced at the sensing points as a pressure distribution graph. It is contemplated that the pressure distribution graph can be a three-dimensional plot or a two-dimensional intensity plot wherein various colors correspond to particular load values. It is further contemplated that the computer can be configured to display the pressure distribution graph substantially in real-time. In still a further aspect, the computer can be configured to store the load calculations for the plurality of sensing points for future analysis and graphical display.

In one aspect, the electrically conductive composite material can be located at the contact surface of the sensor for obtaining surface contact data. If desired, the sensor can include composite material that can be confined within the sensor, at a depth below the contact surface, in order to obtain internal stress data.

The electrically conductive composite material described herein can, in one particular aspect, be formed by mixing a polymer in particulate form with a conductive filler in particulate form. According to this aspect, in order to completely coat the polymer granules with the granules of the conductive filler, the granule size of the polymer can be at least about two orders of magnitude larger than the granule size of the conductive filler. For example, the average granule size of the polymer can, in one aspect, be between about 50 µm and about 500 µm. The average granule size of the conductive filler can be, for example, between about 10 nm and about 500 nm.

Following a mixing step, the composite conductive material can be formed into the sensor shape either with or without areas of non-conductive material in the sensor, as desired, by, for example, compression molding, RAM extrusion, or injection molding. If desired, a curvature can be formed into the contact surface of the sensor in the molding step or optionally in a secondary forming step such as a machining or cutting step.

During use, the sensors of the invention can be located in association with a member so as to form a contact junction between a surface of the member and the contact surface of the sensor. The sensor can then be placed in electrical communication with a data acquisition terminal, for example via a fixed or unfixed hard-wired or a wireless communication circuit, and data can be gathered concerning contact between the sensor and the member. In one particular aspect, dynamic contact data can be gathered. For example, any or all of contact stress data, internal stress data, load, impact data, lubrication regime data, and/or information concerning wear, such as wear mode information can be gathered.

In another aspect, the disclosed sensors can be integrated with the part that they have been designed to replicate and actually used in the joint in the desired working setting. For example, the contact sensor can gather data while functioning as a bearing of a joint or junction in real time in an industrial, medical, or other working setting.

In one aspect, the disclosed sensors can use similar materials as those found in an artificial knee implant. In this aspect, it is contemplated that the tibial inserts of the knee implant can be formed with at least one sensor. It is contemplated that the tibial insert can be implanted with the knee implant, which provides for operative sensing during and after the implantation procedure, or, optionally, it is contemplated that the tibial insert can be a trial insert. In this latter instance, the trial tibial insert can be inserted so that the soft tissue balancing can be accomplished with active force/pressure feedback on the joint. After the balancing is complete, an implantable tibial insert, of the same dimensions of the trial tibial insert, can replace the trail tibial insert within the implant. In this aspect, the trial tibial inserts comprising the sensing technology described herein are able to quantify the force being applied to each side of the implant, thereby allowing surgeons to carry out the important step of soft tissue balancing more precisely and reducing the rate of early failure of artificial knees joints.

It is contemplated that the devices and methodologies described herein are applicable not only for knee repair, reconstruction or replacement surgery, but also repair, reconstruction or replacement surgery in connection with any other joint of the body, as well as any other medical procedure where it is useful to monitor loading on implant surfaces and to display and output data regarding the loads imposed thereon the implantable prosthesis for use in performance of the procedure.

BRIEF DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

DEFINITIONS OF TERMS

Figure 1:
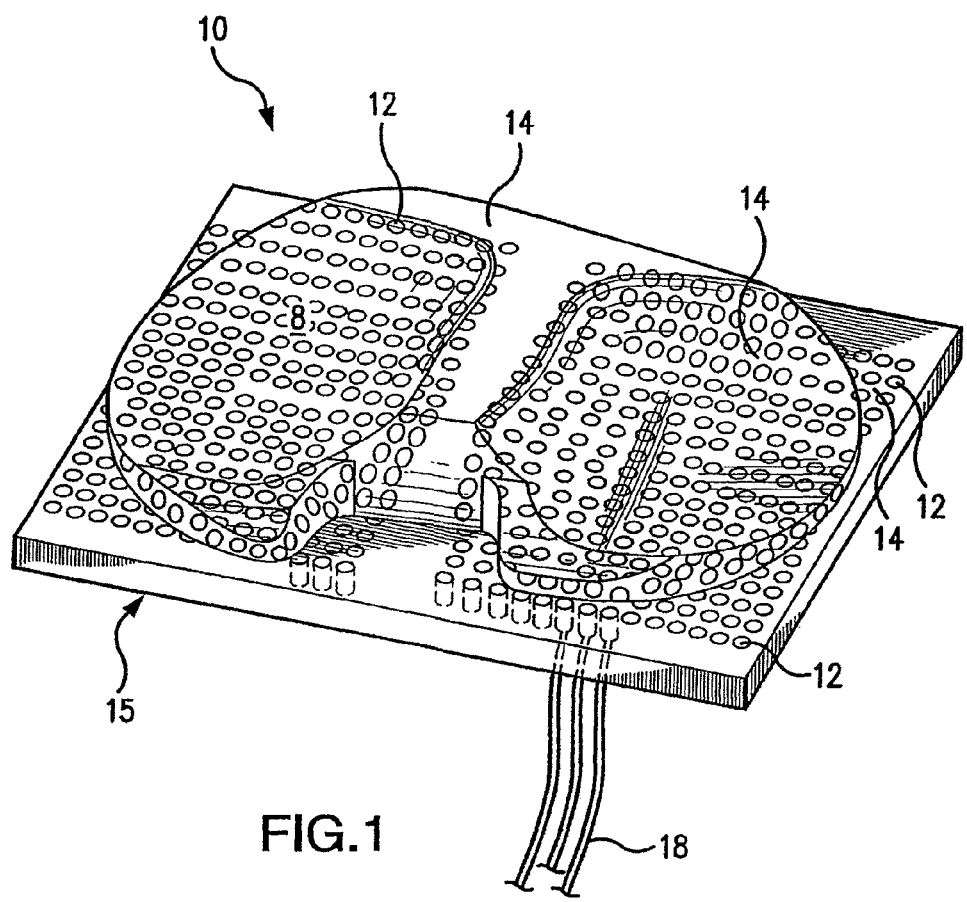
FIG. 1 illustrates one aspect of the sensor disclosed herein for obtaining surface contact data of a junction.

For purposes of the present disclosure, the following terms are herein defined as follows:

The term "static position" is intended to refer to the position of a contact surface of a sensor as described herein at which the contact surface is in equilibrium with adjacent elements within a joint or junction. In the static position, the contact surface will be substantially stationary relative to adjacent joint elements such that any variation in the load applied by a joint element to the contact surface will be detected by the sensor. When a contact surface is supported by a substantially rigid material, the contact surface will typically be in equilibrium with the substantially rigid material, and thus be in the static position, upon contact between the contact sensor and the substantially rigid material. However, when a contact surface is supported by a substantially flexible material, the contact surface will typically be in equilibrium, and thus be in the static position, upon the flexible material reaching its maximum deformation resulting from application of a load to the contact surface.

The term "primary particle" is intended to refer to the smallest particle, generally spheroid, of a material such as carbon black.

The term "aggregate" is intended to refer to the smallest unit of a material, and in particular, of carbon black, found in a dispersion. Aggregates of carbon black are generally considered indivisible and are made up of multiple primary particles held together by strong attractive or physical forces.

The term "granule" is also intended to refer to the smallest unit of a material found in a dispersion. However, while a granule can also be an aggregate, such as when considering carbon black, this is not a requirement of the term. For example, a single granule of a polymer, such as UHMWPE or conventional grade polyethylene, for example can be a single unit.

The term "agglomeration" is intended to refer to a configuration of a material including multiple aggregates or granules loosely held together, as with Van der Waals forces. Agglomerations of material in a dispersion can often be broken down into smaller aggregates or granules upon application of sufficient energy so as to overcome the attractive forces.

The term "conventional polymer" is intended to refer to polymers that have a thermal resistance below about 100° C. and relatively low physical properties. Examples include high-density polyethylene (PE), polystyrene (PS), polyvinyl chloride (PVC), and polypropylene (PP).

The term "engineering polymer" is intended to refer to polymers that have a thermal resistance between about 100° C. and about 150° C. and exhibit higher physical properties, such as strength and wear resistance, as compared to conventional polymers. Examples include polycarbonates (PC), polyamides (PA), polyethylene terephthalate (PET), and ultrahigh molecular weight polyethylene (UHMWPE).

The term "high performance polymer" is intended to refer to polymers that have a thermal resistance greater than about 150° C. and relatively high physical properties. Examples include polyetherether ketone (PEEK), polyether sulfone (PES), polyimides (PI), and liquid crystal polymers (LC).

Contact stress, synonymous with contact pressure, is herein defined as surface stress resulting from the mechanical interaction of two members. It is equivalent to the applied load (total force applied) divided by the area of contact.

Internal stress refers to the forces acting on an infinitely small unit area at any point within a material. Internal stress varies throughout a material and is dependent upon the geometry of the member as well as loading conditions and material properties.

Impact force is herein defined to refer to the time-dependent force one object exerts onto another object during a dynamic collision.

DETAILED DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "sensor" includes aspects having two or more sensors unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes examples where said event or circumstance occurs and examples where it does not.

Presented herein are contact sensors, methods of forming contact sensors, and methods of advantageously utilizing the sensors. In general, contact sensors can be utilized to gather dynamic and/or static contact data at the junction of two opposing members such as a junction found in a joint, a bearing, a coupling, a connection, or any other junction involving the mechanical interaction of two opposing members, and including junctions with either high or low tolerance values as well as junctions including intervening materials between the members, such as lubricated junctions, for example. Dynamic and/or static data that can be gathered utilizing the disclosed sensors can include, for example, load data, lubrication regimes, wear modes, contact stress data, internal stress data, and/or impact data for a member forming the junction. The contact sensors disclosed herein can provide extremely accurate data for the junction being examined, particularly in those aspects wherein at least one of the members forming the junction in the working setting (as opposed, for example, to a testing setting) is formed of a polymeric material.

Beneficially, the sensors described herein can be configured to replicate either one of the mating surfaces forming the junction. Optionally, the sensors described herein can be essentially inflexible when positioned proximate the junction. As such, in a laboratory-type testing application, the sensor can simulate one member forming the junction, and contact data can be gathered for the junction under conditions closer to those expected during actual use, i.e., without altering the expected contact dynamics experienced at the junction during actual use. For example, the disclosed sensors can provide contact data for the junction without the necessity of including extraneous testing material, such as dyes, thin films, or the like, within the junction itself.

In one aspect, the sensor can be formed of a material that essentially duplicates the physical characteristics of the junction member that the sensor is replicating. Accordingly, in this aspect, the sensor can exhibit wear characteristics essentially equivalent to those of the member when utilized in the field, thereby improving the accuracy of the testing data. According to one particular aspect of the invention, rather than being limited to merely simulating a junction-forming member, such as in a pure testing situation, the sensor can be incorporated into the member itself that is destined for use in the working application, i.e., in the field, and can provide contact data for the junction during actual use of the part. It is contemplated that the sensors described herein can be used in a variety of working settings, including, for example and without limitation, in industrial working settings, medical working settings, and the like.

In an additional aspect, the contact sensors disclosed herein can be formed to be substantially non-deformable. Alternatively, the contact sensors disclosed herein can be formed to be substantially deformable. It is further contemplated that the contact sensors can be thermoformed as desired into a three-dimensional shape. In one aspect, it is contemplated that the desired shape of the contact sensors can be a substantially sheet-like member. Optionally, the desired shape of the contact sensors can substantially replicate the three-dimensional shape of a selected structure of a subject's body, including, for example and without limitation, a bone, limb, or other body member. Accordingly, it is contemplated that the contact sensors can be thermoformed to function, for example and without limitation, as prosthetic devices for use as a replacement for, or in conjunction with, the selected structure of the subject's body. It is further contemplated that the desired shape of the contact sensors can substantially replicate the three-dimensional shape of a selected structure outside the body of a subject that is configured to bear loads, including, for example and without limitation, textile devices, vehicle parts and components, anthropomorphic test devices such as crash test dummies, building components, and the like.

In a further aspect, during use of the contact sensors disclosed herein, the contact sensors can be configured to measure a load upon positioning of the contact surface of each contact sensor in a static position. In one aspect, the contact sensors disclosed herein can be formed to be substantially pliable. In this aspect, it is contemplated that the static position can correspond to the contact sensors contacting or abutting a substantially rigid material such that the contact surface of each contact sensor is placed in the static position. For example, a contact sensor can be positioned therebetween two or more substantially rigid conductive elements as described herein such that the contact sensor is in the static position. In another example, the contact sensor can be attached to a substantially rigid insert such that the contact surface is in the static position when the insert is inserted therebetween two or more conductive elements. Alternatively, in another aspect, the contact sensor can be attached to or abut one or more flexible elements as described herein, and the static position can correspond to a state of equilibrium between the elements of a joint, including the contact sensor and the one or more flexible elements. Thus, upon application of a load to a contact surface of a contact sensor within a joint, the contact surface will be placed in the static position when a state of equilibrium is reached within the joint such that the contact surface is substantially stationary relative to adjacent surfaces of other elements of the joint.

In an additional aspect, the contact sensors disclosed herein can be formed to be substantially unpliable. In this aspect, it is contemplated that the static position can correspond to placement of the substantially unpliable contact sensors in any operative position such that the contact sensors can be used as disclosed herein.

As contemplated, in one aspect, changes in resistivity of the contact surface are being measured to determine the applied load or force on the sensor. More particularly, in one aspect, instead of measuring the changes in bulk resistivity of the material forming the sensor, the resistivity changes at the surface of the sensor due to applied loads are being measured. By surface, it is meant the surface portions of the sensor that extend to a depth of about at least 50 nm, to a depth of about at least 100 nm, and, optionally, to a depth of about at least 1,000 nm. In an optional aspect, it is contemplated that the surface portions of the sensor that extend to a depth of less than 50 nm, to a depth of less than 100 nm, and, optionally, to a depth of less than 1,000 nm.

In various aspects, the contact sensors disclosed herein can comprise an electrically conductive composite material that in turn comprises at least one non-conductive polymer material combined with an electrically conductive filler. In another aspect, the composite material disclosed herein can comprise an electrically conductive filler that can provide pressure sensitive electrical conductivity to the composite material, but can do so while maintaining the physical characteristics, e.g., wear resistance, hardness, etc., of the non-conductive polymeric material of the composite. Thus, in this aspect, the sensors disclosed herein can be developed to include a particular polymer or combination of polymers so as to essentially replicate the physical characteristics of the similar but nonconductive polymeric member forming the junction or three-dimensional structure to be examined.

This combination of beneficial characteristics in the composite materials has been attained through recognition and/or development of processes for forming the composite materials in which only a small amount of the electrically conductive filler need be combined with the polymeric material. As such, the physical characteristics of the composite material can more closely resemble those of the starting polymeric material, and the sensor can closely replicate the physical characteristics of a non-conductive polymeric member forming a junction.

This feature can be particularly beneficial when considering the examination of junctions including at least one member formed of engineering and/or high performance polymers. When considering such materials, the addition of even a relatively small amount of additive or filler can drastically alter the physical characteristics that provide the desired performance of the materials. In the past, when attempts were made to form electrically conductive composites of many engineering and high performance polymers, the high levels of additives (greater than about 20% by weight, in most examples) that were required usually altered the physical characteristics of the polymeric material to the point that the formed conductive composite material no longer exhibited the desired characteristics of the starting, non-conductive material. Thus, the examination of junctions formed with such materials has in the past generally required the addition of an intervening material, such as a pressure sensitive film within the junction, leading to the problems discussed above.

It should be noted, however, that while the presently disclosed sensors can be of great benefit when formed to include engineering and/or high performance polymeric composite materials, this is not a requirement of the invention. In other aspects, the polymer utilized to form the composite material can be a more conventional polymer. Regardless of the polymer, copolymer, or combination of polymers that is used to form the disclosed composite conductive materials, the composite materials of the disclosed sensors can exhibit pressure sensitive electrical conductivity and, if desired, can also be formed so as to essentially maintain the physical characteristics of a polymeric material identical to the composite but for the lack of the conductive filler.

In general, any polymeric material that can be combined with an electrically conductive filler to form a pressure sensitive conductive polymeric composite material can be utilized in the contact sensors described herein. For example, various polyolefins, polyurethanes, polyester resins, epoxy resins, and the like can be utilized in the contact sensors described herein. In certain aspects, the composite material can include engineering and/or high performance polymeric materials. In one particular aspect, the composite material can comprise UHMWPE. UHMWPE is generally classified as an engineering polymer, and possesses a unique combination of physical and mechanical properties that allows it to perform extremely well in rigorous wear conditions. In fact, it has the highest known impact strength of any thermoplastic presently made, and is highly resistant to abrasion, with a very low coefficient of friction. The physical characteristics of UHMWPE have made it attractive in a number of industrial and medical applications. For example, it is commonly used in forming polymeric gears, sprockets, impact surfaces bearings, bushings and the like. In the medical industry, UHMWPE is commonly utilized in forming replacement joints including portions of artificial hips, knees, and shoulders. In addition, UHMWPE can be in particulate form at ambient conditions and can be shaped through compression molding or RAM extrusion and can optionally be machined to form a substantially unpliable block (i.e., not easily misshapen or distorted), with any desired surface shape. In another aspect, the composite material can comprise PPS.

Conductive fillers as are generally known in the art can be combined with the polymeric material of choice to form the composite material of the disclosed sensors. The conductive fillers can be, for example and without limitation, carbon black and other known carbons, gold, silver, aluminum, copper, chromium, nickel, platinum, tungsten, titanium, iron, zinc, lead, molybdenum, selenium, indium, bismuth, tin, magnesium, manganese, cobalt, titanium germanium, mercury, and the like.

According to one aspect, a pressure sensitive conductive composite material can be formed by combining a relatively small amount of a conductive filler with a polymeric material. For example, the composite can comprise from between about 0.1% to about 20% by weight of the conductive filler, more preferably from between about 1% to about 15% by weight of the conductive filler, and most preferably from between about 5% to about 12% by weight of the conductive filler. Of course, in other aspects, such as those in which the physical characteristics of the composite material need not approach those of the non-conductive polymeric material, the composite material can include a higher weight percentage of the conductive filler material.

In general, the polymeric material and the conductive filler can be combined in any suitable fashion, which can generally be determined at least in part according to the characteristics of the polymeric material. For example, and depending upon the polymers involved, the materials can be combined by mixing at a temperature above the melting temperature of the polymer (conventional melt-mixing) and the filler materials can be added to the molten polymer, for example, in a conventional screw extruder, paddle blender, ribbon blender, or any other conventional melt-mixing device. The materials can also be combined by mixing the materials in an appropriate solvent for the polymer (conventional solution-mixing or solvent-mixing) such that the polymer is in the aqueous state and the fillers can be added to the solution. Optionally, an appropriate surfactant can be added to the mixture of materials to permit or encourage evaporation of the solvent, resulting in the solid conductive composite material. In another aspect, the materials can be mixed below the melting point of the polymer and in dry form. In this aspect, the materials can be mixed by a standard vortex mixer, a paddle blender, a ribbon blender, or the like, such that the dry materials are mixed together before further processing.

When mixing the components of the composite material, the mixing can be carried out at any suitable conditions. For example, in one aspect, the components of the composite material can be mixed at ambient conditions. In other aspects, however, the components of the composite material can be mixed at non-ambient conditions. It is contemplated that the components of the composite material can be mixed under non-ambient conditions to, for example and without limitation, maintain the materials to be mixed in the desired physical state and/or to improve the mixing process.

When dry mixing the materials to be utilized in the composite, the exact particulate dimensions of the materials are not generally critical to the invention. However, in certain aspects, the relative particulate size of the materials to be combined in the mixture can be important. In particular, the relative particulate size of the materials to be combined can be important in those aspects wherein a relatively low amount of conductive filler is desired and in those aspects wherein the polymer granules do not completely fluidize during processing. For example, the relative particle size can be important in certain aspects wherein engineering or high-performance polymers are utilized. It is contemplated that the relative particle size can be particularly important during utilization of extremely high melt viscosity polymers such as UHMWPE, which can be converted via non-fluidizing conversion processes, including, for example and without limitation, compression molding or RAM extrusion processes.

In such aspects, the particle size of the filler can beneficially be considerably smaller than the particle size of the polymer. According to this aspect, it is contemplated that due to the small size of the conductive filler particles relative to the larger polymer particles, the conductive filler is able to completely coat the polymer during mixing and, upon conversion of the composite polymeric powder in a non-fluidizing conversion process to the final solid form, the inter-particle distance of the conductive filler particles can remain above the percolation threshold such that the composite material can exhibit the desired electrical conductivity. According to this aspect, when forming the composite mixture, the granule or aggregate size of the conductive filler to be mixed with the polymer can be at least about two orders of magnitude smaller than the granule size of the polymer. In some aspects, the granule or aggregate size of the conductive filler can be at least about three orders of magnitude smaller than the granule size of the polymer.

In forming the composite material according to this aspect, a granular polymer can be dry mixed with a conductive filler that is also in particulate form. Readily available UHMWPE can have a granule diameter in a range of from about 50 µm to about 200 µM. Typically, the individual granule can be made up of multiple sub-micron sized spheroids and nano-sized fibrils surrounded by varying amounts of free space.

In one aspect, the conductive filler for mixing with the polymer can comprise carbon black. Carbon black is readily available in a wide variety of agglomerate sizes, generally having diameters ranging from about 1 µm to about 100 µm. It is contemplated that these agglomerates can be broken down into smaller aggregates having diameters ranging from about 10 nm to about 500 nm upon application of suitable energy.

Upon dry mixing of the particulate conductive filler and the larger particulate polymer material with suitable energy, the smaller granules of conductive filler material can completely coat the larger polymer granules. For example, a single powder particle can be obtained following mixing of 8 wt % carbon black with 92 wt % UHMWPE. It is contemplated that the UHMWPE particles can be completely coated with carbon black aggregates. It is further contemplated that the combination of mixing forces with electrostatic attractive forces existing between the non-conductive polymeric particles and the smaller conductive particles is primarily responsible for breaking the agglomerates of the conductive material down into smaller aggregates and forming and holding the coating layer of the conductive material on the polymer particles during formation of the composite powder, as well as during later conversion of the powdered composite material into a solid form.

Following formation of the mixture comprising the conductive filler and the polymeric material, the mixture can be converted as desired to form a solid composite material. In one aspect, the solid composite material can be electrically conductive. The solid composite material thus formed can also maintain the physical characteristics of the polymeric material in mixtures comprising a relatively low weight percentage of conductive filler. For example, in the aspect described above, in which the composite material includes a conductive filler mixed with UHMWPE, the powder can be converted via a compression molding process or a RAM extrusion process, as is generally known in the art. Optionally, following conversion of the powder, the resultant solid molded material can be machined to produce a desired curvature on at least one contact surface.

In other aspects however, and primarily depending upon the nature of the polymeric portion of the composite, other conversion methods may preferably be employed. For example, in other aspects, the polymeric portion of the composite material can be a polymer, a co-polymer, or a mixture of polymers that can be suitable for other converting processes. For example and without limitation, the composite polymeric material can be converted via a conventional extrusion or injection molding process.

The composite material of the disclosed sensors can optionally comprise other materials in addition to the primary polymeric component and the conductive filler discussed above. In one aspect, the composite material can comprise additional fillers, including, for example and without limitation, various ceramic fillers, aluminum oxide, zirconia, calcium, silicon, fibrous fillers, including carbon fibers and/or glass fibers, or any other fillers as are generally known in the art. In another aspect, the composite material can include an organic filler, including for example and without limitation, tetrafluoroethylene or a fluororesin. In this aspect, it is contemplated that the organic filler can be added to improve sliding properties of the composite material.

It is believed that during the conversion process, the polymer particles can fuse together and confine the conductive filler particles to a three-dimensional channel network within the composite, forming a segregated network type of composite material. In operation, the distance between individual carbon black primary particles and surrounding small aggregates can be about 10 nm. It is contemplated that when two conductive filler particles are within about 10 nm of each other, the conductive filler particles can conduct current via electron tunneling, or percolation, with very little resistance. Thus, many conductive paths fulfilling these conditions can exist within the composite material. Moreover, when deformable polymers are used, the conductivity, and in particular the resistance, of the composite material of the contact sensors described herein can vary upon application of a compressive force (i.e., load) to the composite material.

Accordingly, following any desired molding, shaping, cutting and/or machining and also following any desired physical combination of the formed composite material with other non-conductive materials (various aspects of which are discussed further below), the composite materials of the contact sensors described herein, which comprise at least one conductive filler, can be formed into the sensor shape and placed in electrical communication with a data acquisition terminal.

For example, in one aspect, the composite material of the sensor can be connected to a data acquisition terminal. In this aspect, the composite material can be connected to the data acquisition terminal by, for example and without limitation, conventional alligator clips, conductive epoxy, conductive silver ink, conventional rivet mechanisms, conventional crimping mechanisms, and other conventional mechanisms for maintaining electrical connections. In another aspect, the composite material can be machined to accept a connector of a predetermined geometry within the composite material itself. Other connection regimes as are generally known in the art may optionally be utilized, however, including fixed or unfixed connections to any suitable communication system between the composite material and the data acquisition terminal. No particular electrical communication system is required of the contact sensors described herein. For example, in some aspects, the electrical communication between the composite material and the data acquisition terminal can be wireless, rather than a hard wired connection.

In one aspect, the data acquisition terminal can comprise data acquisition circuitry. In another aspect, the data acquisition terminal can comprise at least one multiplexer placed in electrical communication with a microcontroller via the data acquisition circuitry. In an additional aspect, the data acquisition circuitry can comprise at least one op-amp for providing a predetermined offset and gain through the circuitry. In this aspect, the at least one op-amp can comprise a converting op-amp configured to convert a current reading into a voltage output. It is contemplated that the converting op-amp can measure current after it has passed through the at least one multiplexer and then convert the measured current into a voltage output. In a further aspect, the data acquisition terminal can comprise an Analog/Digital (AM) converter. In this aspect, the A/D converter can be configured to receive the voltage output from the converting op-amp. It is contemplated that the A/D converter can convert the voltage output into a digital output signal. In yet another aspect, the data acquisition terminal can be in electrical communication with a computer having a processor. In this aspect, the computer can be configured to receive the digital output signal from the A/D converter. It is contemplated that the A/D converter can have a conventional Wi-Fi transmitter for wirelessly transmitting the digital output signal to the computer. It is further contemplated that the computer can have a conventional Wi-Fi receiver to receive the digital output signal from the A/D converter.

Figure 5:
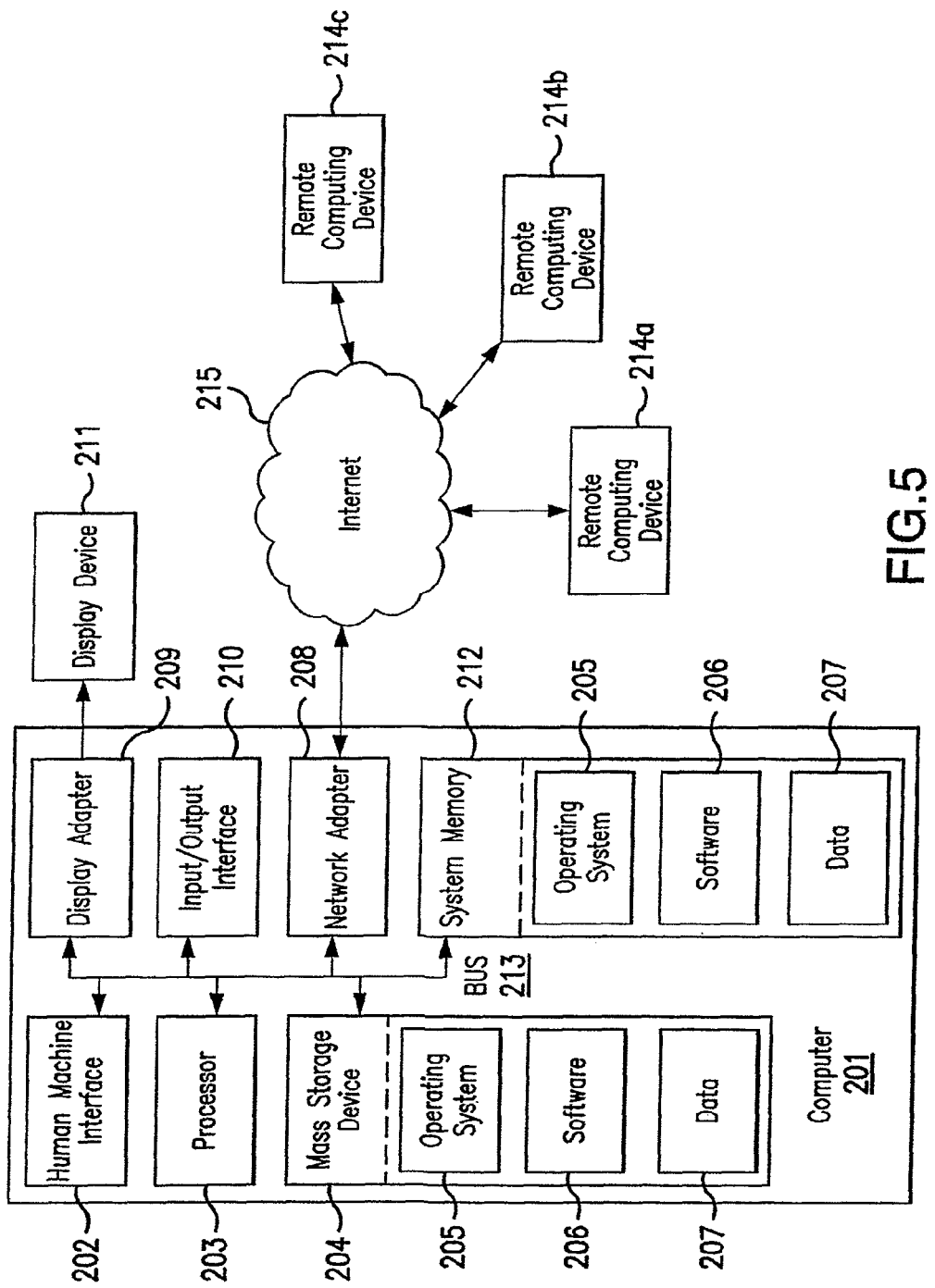
FIG. 5 illustrates a simplified, non-limiting block diagram showing select components of an exemplary operating environment for performing the disclosed methods.

As electrical communications methods and electrical data analysis methods and systems are generally known in the art, these particular aspects of the disclosed contact sensor systems are not described in great detail herein. FIG. 5 is a block diagram illustrating an exemplary operating environment for performing the disclosed methods and portions thereof. This exemplary operating environment is only an example of an operating environment and is not intended to suggest any limitation as to the scope of use or functionality of operating environment architecture. Similarly, the operating environment contemplated for the contact sensors disclosed herein should not be interpreted as having any dependency or requirement relating to any one component or combination of components illustrated in the exemplary operating environment.

The present methods and systems can be operational with numerous other general purpose or special purpose computing system environments or configurations. Examples of well known computing systems, environments, and/or configurations that can be suitable for use with the system and method comprise, but are not limited to, personal computers, server computers, laptop devices, hand-held electronic devices, vehicle-embedded electronic devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed system and method can be described in the general context of computer-executable instructions, such as program modules, being executed by one or more computers or other devices. Generally, program modules comprise computer code, routines, programs, objects, components, data structures, etc. that perform particular tasks or implement particular abstract data types. In one aspect, the program modules can comprise a system control module. The disclosed method can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the system and method disclosed herein can be implemented via a general-purpose computing device in the form of a computer 200. As schematically illustrated in FIG. 5, the components of the computer 200 can comprise, but are not limited to, one or more processors or processing units 203, a system memory 212, and a system bus 213 that couples various system components including the processor 203 to the system memory 212.

The system bus 213 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI) bus also known as a Mezzanine bus. The bus 213, and all buses specified in this description can also be implemented over a wired or wireless network connection and each of the subsystems, including the processor 203, a mass storage device 204, an operating system 205, contact sensor software 206, contact sensor data 207, a network adapter 208, system memory 212, an Input/Output Interface 210, a display adapter 209, a display device 211, and a human machine interface 202, can be contained within one or more remote computing devices 214a,b,c at physically separate locations, connected through buses of this form, in effect implementing a fully distributed system.

The computer 200 typically comprises a variety of computer readable media. Exemplary readable media can be any available media that is accessible by the computer 200 and comprises, for example and without limitation, both volatile and non-volatile media, removable and non-removable media. The system memory 212 can comprise computer readable media in the form of volatile memory, such as random access memory (RAM), and/or non-volatile memory, such as read only memory (ROM). The system memory 212 typically contains data such as pressure and/or hysteresis data 207 and/or program modules such as operating system 205 and contact sensor module software 206 that are immediately accessible to and/or are presently operated on by the processing unit 203.

In another aspect, the computer 200 can also comprise other removable/non-removable, volatile/non-volatile computer storage media. By way of example, FIG. 5 illustrates a mass storage device 204 which can provide non-volatile storage of computer code, computer readable instructions, data structures, program modules, and other data for the computer 200. For example and without limitation, a mass storage device 204 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 204, including by way of example, an operating system 205 and contact sensor module software 206. It is contemplated that both the operating system 205 and the contact sensor module software 206 can comprise at least some elements of the programming. Pressure and/or hysteresis data 207 can also be stored on the mass storage device 204. Pressure and/or hysteresis data 207 can be stored in any of one or more databases known in the art. Examples of such databases comprise, DB2®, Microsoft® Access, Microsoft® SQL Server, Oracle®, mySQL, PostgreSQL, and the like. The databases can be centralized or distributed across multiple systems.

In another aspect, the user can enter commands and information into the computer 200 via an input device (not shown). It is contemplated that the input device can comprise, for example and without limitation, a keyboard, pointing device (e.g., a "mouse"), a microphone, a joystick, a scanner, tactile input devices such as gloves and other body coverings, and the like. These and other input devices can be connected to the processing unit 203 via a human machine interface 202 that is coupled to the system bus 213. However, it is contemplated that the input devices can be connected to the processing unit 203 by other interface and bus structures, including, for example and without limitation, a parallel port, game port, an IEEE 1394 Port (also known as a Firewire port), a serial port, and a universal serial bus (USB).

In yet another aspect, a display device 211 can also be connected to the system bus 213 via an interface, such as a display adapter 209. It is contemplated that the computer 200 can have more than one display adapter 209 and the computer 200 can have more than one display device 211. For example, a display device can be a monitor, an LCD (Liquid Crystal Display), or a projector. In addition to the display device 211, other output peripheral devices can comprise components such as a printer (not shown) which can be connected to the computer 200 via Input/Output Interface 210.

The computer 200 can operate in a networked environment using logical connections to one or more remote computing devices 214a,b,c. By way of example, a remote computing device can be a personal computer, portable computer, a server, a router, a network computer, a peer device or other common network node, and the like. Logical connections between the computer 200 and a remote computing device 214a,b,c can be made via a local area network (LAN) and a general wide area network (WAN). Such network connections can be through a network adapter 208. A network adapter 208 can be implemented in both wired and wireless environments. Such networking environments are conventional and commonplace in offices, enterprise-wide computer networks, intranets, and the Internet 215.

For purposes of illustration, application programs and other executable program components such as the operating system 205 are illustrated herein as discrete blocks, although it is recognized that such programs and components reside at various times in different storage components of the computing device 200, and are executed by the data processor(s) of the computer. An implementation of contact sensor software 206 can be stored on or transmitted across some form of computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any method or technology for storage of information such as computer readable instructions, data structures, program modules, or other data. Exemplary computer storage media can comprise, for example and without limitation, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In various aspects, it is contemplated that the methods and systems described herein can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. expert inference rules generated through a neural network or production rules from statistical learning).

It is contemplated that the contact sensors described herein can optionally comprise one or more sensing points. In one aspect, the contact sensor can include only a single sensing point. For example, the entire contact surface of the disclosed sensors can be formed of the conductive composite material. According to this aspect, the contact sensors can be utilized to obtain impact data and/or the total load on the contact surface at any time. Such an aspect can be preferred, for example, in order to obtain total load or impact data for a member without the necessity of having external load cells or strain gauges in communication with the load-bearing member. This sensor type may be particularly beneficial in those aspects wherein the sensor is intended to be incorporated with or as the member for use in the field. For example, any polymeric load-bearing member utilized in a process could be formed from the physically equivalent but conductive composite material as described herein and incorporated into the working process to provide real time wear and load data of the member without diminishing the wear performance of the member due to the acquisition of conductive capability.

In other aspects, the sensors disclosed herein can include a plurality of sensing points and can provide more detailed data about the junction or the members forming the junction. For example, the plurality of sensing points can provide data describing the distribution of contact stresses and/or internal stresses, data concerning types of wear modes, or data concerning a lubrication regime as well as load and impact data for a member forming a junction. According to this aspect, the composite material can be located at predetermined, discrete regions of a sensor to form the plurality of sensing points on or in the sensor, and a non-conductive material can separate the discrete sensing points from one another. Data from the plurality of discrete sensing points can then be correlated and analyzed and can provide information concerning, for example, the distribution of contact characteristics across the entire mating surface, and in particular can provide contact information under dynamic loading conditions involving, for example, sliding, rolling, or grinding motions across the surface of the sensor.

It is contemplated that the plurality of sensing points can be arranged in any desired configuration along a surface of the sensor. For example, and without limitation, the sensing points can be positioned in a series of parallel rows. Alternatively, the sensing points can be positioned in staggered or overlapping configurations. In one aspect, the sensing points can be substantially evenly spaced. In another aspect, the sensing points can be substantially unevenly spaced.

It is contemplated that selected sensing points among the plurality of sensing points can be activated during the application of a load while the remainder of the sensing points remain deactivated.

FIG. 1 is a schematic diagram of one aspect of the sensor as disclosed herein, including a plurality of sensing points at the contact surface of the junction member. Surface sensing points such as those in this aspect can be utilized to determine contact surface data, including, for example and without limitation, contact stress data, lubrication data, impact data, and information concerning wear modes. The polymeric sensor 10 includes a contact surface 8 for contact with an electrically conductive joint element (not shown) to simulate the dynamic characteristics of the joint formed between the sensor and the conductive joint element. In this particular aspect, the contact surface 8 defines a curvature to simulate that of the tibial plateau of an artificial knee implant. It is contemplated that the conductive joint element can be metallic.

As can be seen with reference to FIG. 1, the sensor 10 includes a plurality of sensing points 12 at the contact surface 8 of the sensor 10. The sensing points 12 can be formed of the conductive composite material as herein described. Thus, unlike conventional contact sensors, the conductive composite material functions as not only the sensing material, but also as an electrical communication pathway. After a load is applied to the sensor 10 and the contact surface 8 is positioned in the static position, each sensing point 12 is configured to produce an output signal in response to the change in resistance experienced by the conductive composite material at the contact surface proximate the sensing point.

In one aspect, because the conductive composite material provides electrical communication between the sensing points at the contact surface of the sensor, the conductive composite material of each sensor can have a bulk resistance. In this aspect, the bulk resistance can be measured in Ohms per unit length; accordingly, as the length of the sensor increases, the bulk resistance proportionally increases. Therefore, the bulk resistance of the conductive composite material varies from one sensing point to another sensing point. It is contemplated that the farther a particular sensing point is from an electrical connection between the sensor and the data acquisition terminal, the greater the bulk resistance will be at that particular sensing point. Consequently, it is contemplated that the resistance measured at each sensing point will be different even when the change in resistance at some sensing points is identical. In addition, it is contemplated that the sensing points can always have at least some level of electrical communication with adjacent sensing points, even when a load is not being applied. Thus, when a load is applied to one or more sensing points, the sensing points that are subjected to the load can generate current within sensing points that are not subjected to the load, thereby creating parallel resistance paths.

In order to account for the bulk resistance of the composite material and the parallel resistance paths described herein, the processor of the computer disclosed herein can be programmed to accurately determine the actual change in contact resistance experienced at each sensing point of the sensor based on the digital output signal received from the A/D converter of the data acquisition terminal. In one aspect, the processor can be configured to calculate contact resistance changes at individual sensing points based on the current measurements at each respective sensing point. In this aspect, the processor can calculate the resistance changes as the solution to a series of non-linear equations that describe the load in terms of the current measurements at each respective sensing point. It is contemplated that the processor can be configured to solve the series of simultaneous non-linear equations using one or more conventional algorithms, including, for example and without limitation, the "Newton-Raphson method" and the "node analysis" method. The contact resistance changes calculated by the processor can then be used to determine the actual applied load at each respective sensing point.

Thus, in contrast to conventional thin-film load and pressure sensors which calculate loads based on changes in bulk resistance through the depth of the sensor, the contact sensors disclosed herein can calculate loads based on the surface contact characteristics at a junction formed between two electrically conductive members. Specifically, when the electrically conductive members are substantially rigid, a contact sensor as disclosed herein can abut or contact the electrically conductive members such that the contact surface of the contact sensor is in the static position.

In one exemplary aspect, in use, after the contact surface of the contact sensor is positioned in the static position therebetween the electrically conductive members, the contact sensor will measure a contact resistance that varies with the load applied to the contact surface. Because the contact surface of the contact sensor is substantially in a static position, as a conductive member applies a load to the contact surface of the contact sensor, the total surface area of the contact sensor that is in contact with the conductive member will gradually increase as the applied load increases. As this surface contact area increases, the contact resistance across the contact surface of the contact sensor will decrease, thereby increasing the current within the contact sensor (assuming a constant applied voltage). Accordingly, the contact sensors disclosed herein are configured to detect variations in the electrical signal created by contact between one or more conductive members and the electrically conductive composite material of the contact sensors. These variations in the electrical signal correspond to variations in the load applied to the contact sensor by the conductive members.

In yet another aspect, the conductive polymer composite can have a thickness ranging from about 0.003 in. to about 0.03 in., resulting in an overall flexible form of the conductive polymer composite. It is contemplated that, although the conductive polymer composite is relatively thin and flexible, the surface of this conductive polymer composite can behave in substantially the same manner as the surface of a substantially rigid conductive polymer composite as described herein. Therefore, it is contemplated that when the thin, flexible conductive polymers disclosed herein are sandwiched between two thin and flexible conductive members, the total surface area of the contact surface of the thin, flexible conductive polymer composite that is in contact with the conductive members can increase as an increasing load is applied to one or more of the thin and flexible sensors. Therefore, it is contemplated that the changes in the surface resistivity of the material forming the thin, flexible sensor can be measured for the thin, flexible polymer composite in the same manner as the substantially rigid conductive polymer composite. By surface, it is meant the surface portions of the sensor that extend to a depth of about at least 50 nm, to a depth of about at least 100 nm, and, optionally, to a depth of about at least 1,000 nm, in the same manner as the contact surfaces of thicker, substantially rigid conductive polymer composites as described herein. In an optional aspect, In an optional aspect, it is contemplated that the surface portions of the sensor that extend to a depth of less than 50 nm, to a depth of less than 100 nm, and, optionally, to a depth of less than 1,000 nm.

It is contemplated that the conductive paths produced by the plurality of sensing points can vary depending on the spatial arrangement of the sensing points. For example, the conductive paths produced by sensing points in a parallel and evenly spaced configuration can be substantially different than the conductive paths produced when the sensing points are positioned in overlapping, staggered, or unevenly spaced configurations.

In use, and with reference to FIG. 1, after the contact surface 8 of the sensor 10 is positioned in the static position, upon contact of a single sensing point 12 with the electrically conductive joint element, an electrical signal can be generated and sent via wire 18 to a data acquisition terminal as described herein. In one aspect, this electrical signal can be sent in response to a voltage excitation signal that is processed to the electrical signal by the data acquisition terminal. As one skilled in the art will appreciate, in this example, the joint element can act as a first electrode that is mechanically and electrically coupled to the polymeric composite material, which is in turn electrically coupled to a second electrode, i.e., the wire 18. The electrically coupled respective first and second electrodes and the polymeric composite material form an electrical circuit. Though not expressly shown in the Figure, in this particular aspect, each sensing point 12 of the plurality of sensing points can be wired so as to provide data from that point to the data acquisition terminal. It is contemplated that the characteristics of the generated electrical signal can vary with the load applied to the contact surface proximate the sensing point 12, and a dynamic contact stress distribution profile for the joint can thereby be developed.

The surface area and geometry of any individual sensing point 12 as well as the overall geometric arrangement of the plurality of sensing points 12 over the contact surface 8 of the sensor 10, can be predetermined as desired. For example, through the formation and distribution of smaller sensing points 12 with less intervening space between individual sensing points 12, the spatial resolution of the data can be improved. While there may be a theoretical physical limit to the minimum size of a single sensing point determined by the size of a single polymer granule, practically speaking, the minimum size of the individual sensing points will only be limited by modern machining and electrical connection forming techniques. In addition, increased numbers of data points can complicate the correlation and analysis of the data. As such, the preferred geometry and size of the multiple sensing points can generally involve a compromise between the spatial resolution obtained and complication of formation methods.

In this particular aspect as seen in FIG. 1, the composite material forming the surface sensing points 12 can extend to the base 15 of the sensor 10, where electrical communication can be established to a data acquisition and analysis module, such as a computer with suitable software, for example.

In one aspect, the discrete sensing points 12 of the sensor 10 of FIG. 1 can be separated by a non-conductive material 14 that can, in one aspect, be formed of the same polymeric material as that contained in the composite material forming the sensing points 12. In general, the method of combining the two materials to form the sensor can be any suitable formation method. For example, in one aspect the composite material can be combined with a virgin material to produce one or more sensor sheets as described herein. Alternatively, the composite material can be formed into a desired shape, such as multiple individual rods of composite material as shown in the aspect illustrated in FIG. 1, and then these discrete sections can be inserted into a block of the non-conductive polymer that has had properly sized holes cut out of the block. Optionally, the two polymeric components of the sensor can then be fused, such as with heat and/or pressure, and any final shaping of the two-component sensor, such as surface shaping via machining, for example, can be carried out so as to form the sensor 10 including discrete sensing points 12 formed of the conductive composite material at the surface 8.

In many aspects of the invention, the same material, but for the presence or absence of the conductive filler, can be used for the composite sensing points 12 and the intervening spaces 14 since, as described above, the physical characteristics of the composite material can be essentially identical to the physical characteristics of the non-conductive material used in forming the composite. According to this aspect, the sensor 10 can have uniform physical characteristics across the entire sensor 10, i.e., both at the sensing points 12 and in the intervening space 14 between the sensing points.

In one particular aspect, the polymer used to form the sensor 10 can be the same polymer as is used to form the member for use in the field. For example, when considering the examination of artificial joints, the polymer used to form both the composite material at the sensing points 12 and the material in the intervening space 14 between the sensing points 12 can be formed of the same polymer as that expected to be used to form a polymeric bearing component of an implantable device (e.g., UHMWPE or PPS). Thus, the sensor 10 can provide real-time, accurate, dynamic contact data for the implantable polymeric bearing under expected conditions of use.

Optionally, the surface 8 of the sensor 10 can be coated with a lubricating fluid, and in particular, a lubricating fluid such as can be utilized for the bearing component of the implantable device during actual use and under the expected conditions of use (e.g., pressure, temperature, etc.). In this aspect, in addition to providing direct contact data, the disclosed sensors can also be utilized to examine data concerning contact through an intervening material, i.e., lubrication regimes under expected conditions of use. For example, the sensor can be utilized to determine the type and/or quality of lubrication occurring over the contact surface of the sensor, including variation in fluid film thickness across the surface during use. In one aspect, this can merely be determined by presence or absence of fluid, e.g., presence or absence of direct contact data (i.e., current flow) in those aspects wherein the fluid is a non-conductive lubricating fluid. In other aspects, a more detailed analysis can be obtained, such as determination of variation in fluid film thickness. This information can be obtained, for example, by comparing non-lubricated contact data with the data obtained from the same joint under the same loading conditions but including the intervening lubricant. In another aspect, such information could be obtained through analysis of the signal obtained upon variation of the frequency and amplitude of the applied voltage. In yet another aspect, the sensor can be utilized in a capacitance mode, in order to obtain the exact distance between the two surfaces forming the joint. In one particular aspect, the disclosed sensor can be utilized to determine a lubrication distribution profile of the contact surface over time.

Figure 2:
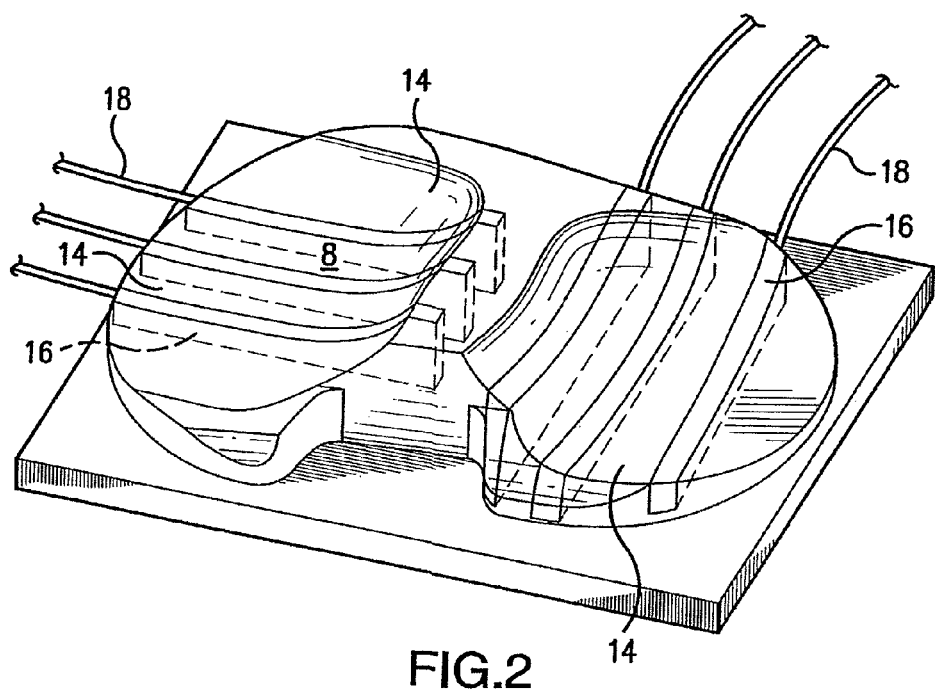
FIG. 2 illustrates another aspect of the sensor disclosed herein for obtaining surface contact data of a junction.
Figure 3:
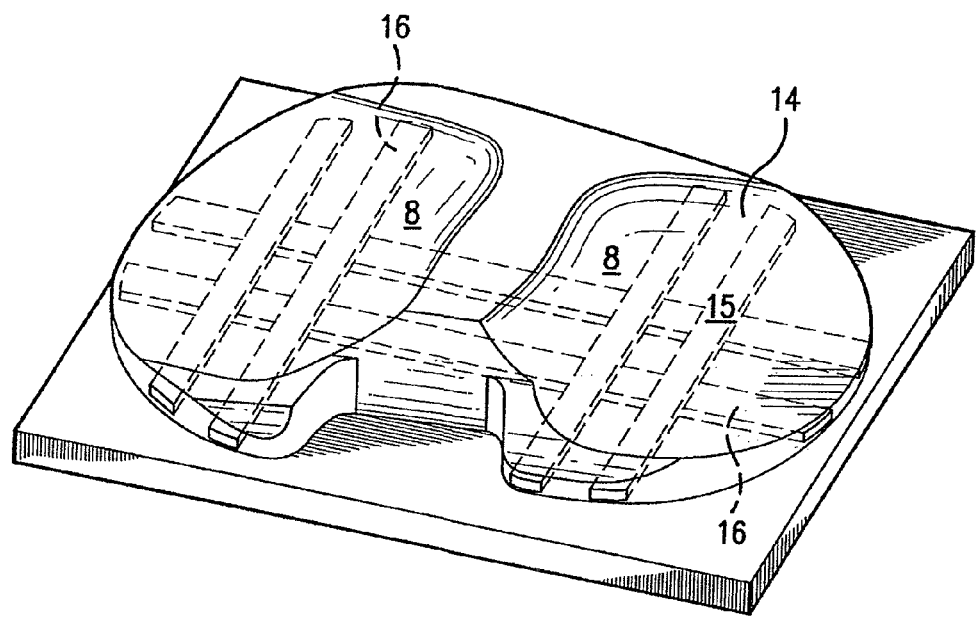
FIG. 3 illustrates another aspect of the sensor disclosed herein for obtaining sub-surface contact data of a junction.

FIG. 2 illustrates another aspect of the contact sensors as described herein. According to this aspect, the sensor 10 includes multiple sensing strips 16 across the contact surface 8 of the sensor. As illustrated, in this aspect, the orientations of the individual sensing strips 16 across the different condoyles formed on the contact surface can be selectively varied. Alternatively, and as shown in FIG. 3, strips can be laid in different orientations on separate but identically shaped sensors in a multi-sensor testing apparatus. In any case, by varying the orientation of sensor strips on multiple, but essentially identical surfaces, virtual cross-points can be created when the data from the different surfaces is correlated. In particular, when contacts of the same shape and magnitude at the same location of different surfaces are recognized, a virtual data point at the cross-point can be created. As can be seen in FIG. 3, this aspect can allow the formation of fewer electrical connections and wires 18 in order to provide data to the acquisition and analysis location, which may be preferred in some aspects due to increased system simplicity.

Optionally, it is contemplated that the contact sensors as described herein can be utilized to provide sub-surface stress data. For example, in the aspect illustrated in FIG. 3, multiple sensing strips 16 can be located within a subsurface layer at a predetermined depth of the sensor. According to this aspect, the horizontal and vertical strips 16 can cross each other with a conductive material located between the cross points to form a subsurface sensing point 15 at each cross point. In one aspect, the strips 16 can be formed of the composite material described herein with the intervening material being the same basic composite material but with a lower weight percentage of the conductive filler, and the layer can be laid within the insulating non-conductive polymer material 14. In another aspect, the sensing strips 16 can be any conductive material, such as a metallic wire, for example, laid on either side of a sheet or section of the composite material and the layer can then be located at a depth from the surface 8 of the sensor.

Application of a load at the surface 8 of the sensor can then vary the electronic characteristics at the internal sensing point 15. In particular, the current flow at any sensing point 15 can vary in proportion to the stress at that sensing point. Thus, when data from multiple sensing points 15 are correlated, an internal stress profile for the sensor can be developed at the depth of the sensing points.

Figure 13:
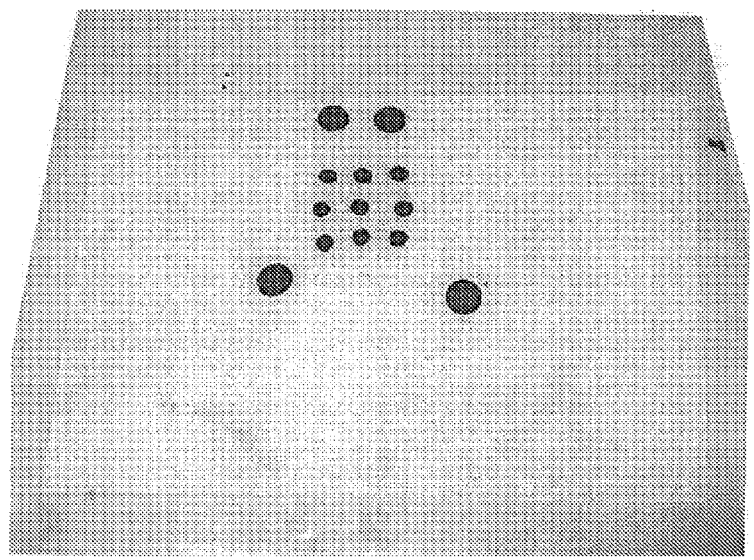
FIG. 13 is a photograph of a sensor sheet according to one aspect disclosed herein, illustrating a plurality of dots comprising a conductive filler.

In yet another aspect, in lieu of strips, the conductive filler may be arranged on the sensor sheet as a plurality of dots, as shown in FIG. 13. In this aspect, there would be reduced opportunity for cross-talk when the sensor sheets were thermoformed into shape. In this aspect, it can be appreciated that the electrical connections necessary to perform the load analysis can be challenging due to the number of connections required. As such, application of current to one of the sheets may be achieved using a sheet of flexible conductive material, such as, for example and without limitation, mesh, foil, and the like. In use, a sensor sheet having a plurality of conductive dots can be configured for coupling with electrodes proximate each respective conductive dot. Following application of a load with a metallic or other conductive element, it is contemplated that current can flow through the conductive filler therein the sensor sheet, thereby permitting calculation of the applied loads.

Figure 14:
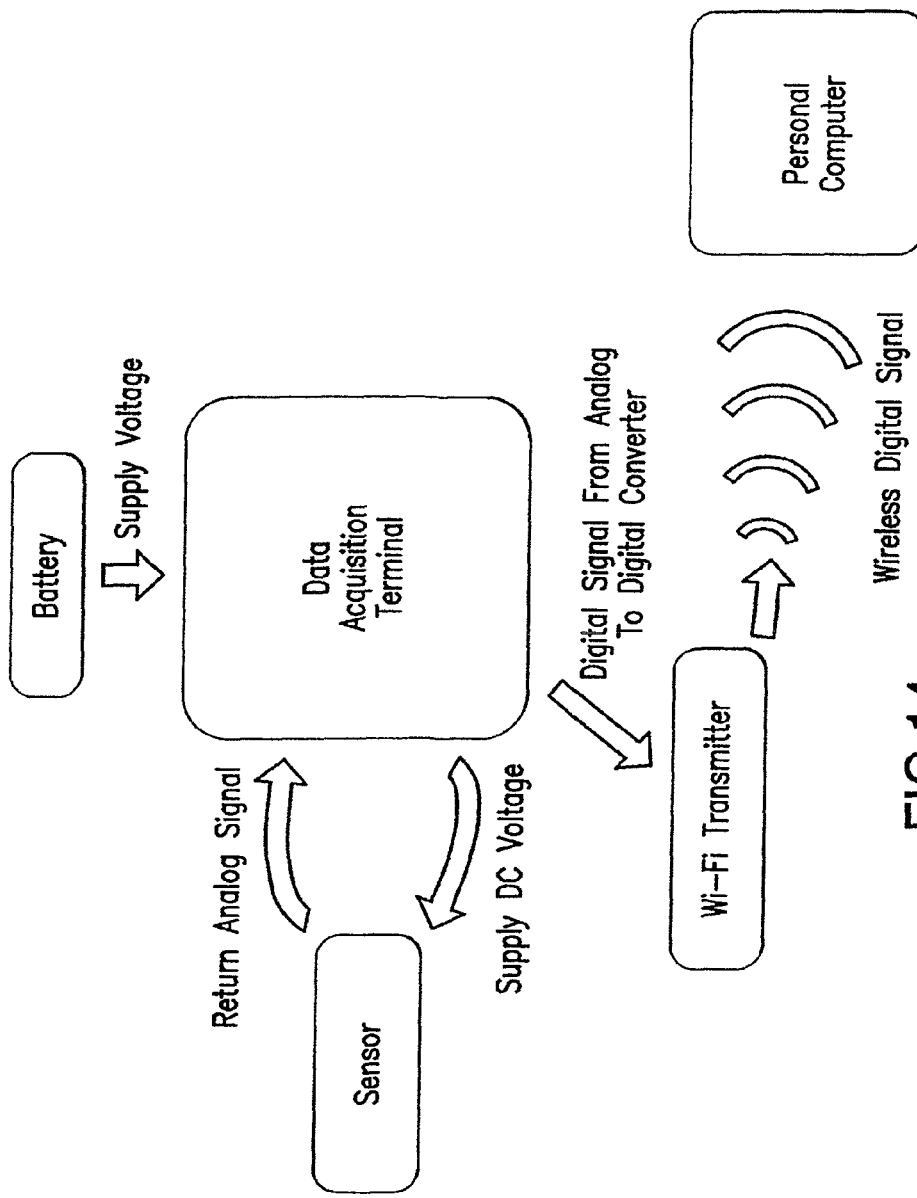
FIG. 14 is a schematic of a contact sensor in operative communication with a data acquisition terminal, and showing a battery operatively coupled to the data acquisition terminal and a computer coupled to the data acquisition terminal via a Wi-Fi transmitter.

FIG. 14 is a schematic of a contact sensor in operative communication with a data acquisition terminal. As depicted in FIG. 14, a battery can be operatively coupled to the data acquisition terminal, and a computer can be coupled to the data acquisition terminal via a Wi-Fi transmitter.

In use, it is contemplated that a plurality of sensor sheets can be thermoformed in substantially identical three-dimensional sizes and orientations. In one aspect, the sensor sheets can be placed in a stacked relationship with adjacent sensor sheets. In this aspect, it is contemplated that no fusing between adjacent sensor sheets will occur. In another aspect, the configurations of the portions of conductive filler therein the sensor sheets can be selected to create overlap between the conductive portions of adjacent sensor sheets. For example, and without limitation, the conductive portions of one sensor sheet can be oriented substantially perpendicularly to the conductive portions of an adjacent sensor sheet prior to stacking of the sensor sheets. It is contemplated that upon application of a load to the sensor sheets, each respective sensor sheet can function as an electrode such that no additional contact with a conductive element is required to produce current therethrough the sensors sheets. It is further contemplated that the overlap between the conductive portions of the sensor sheets can create cross points for measuring loads applied to the sensor sheets.

Figure 4:
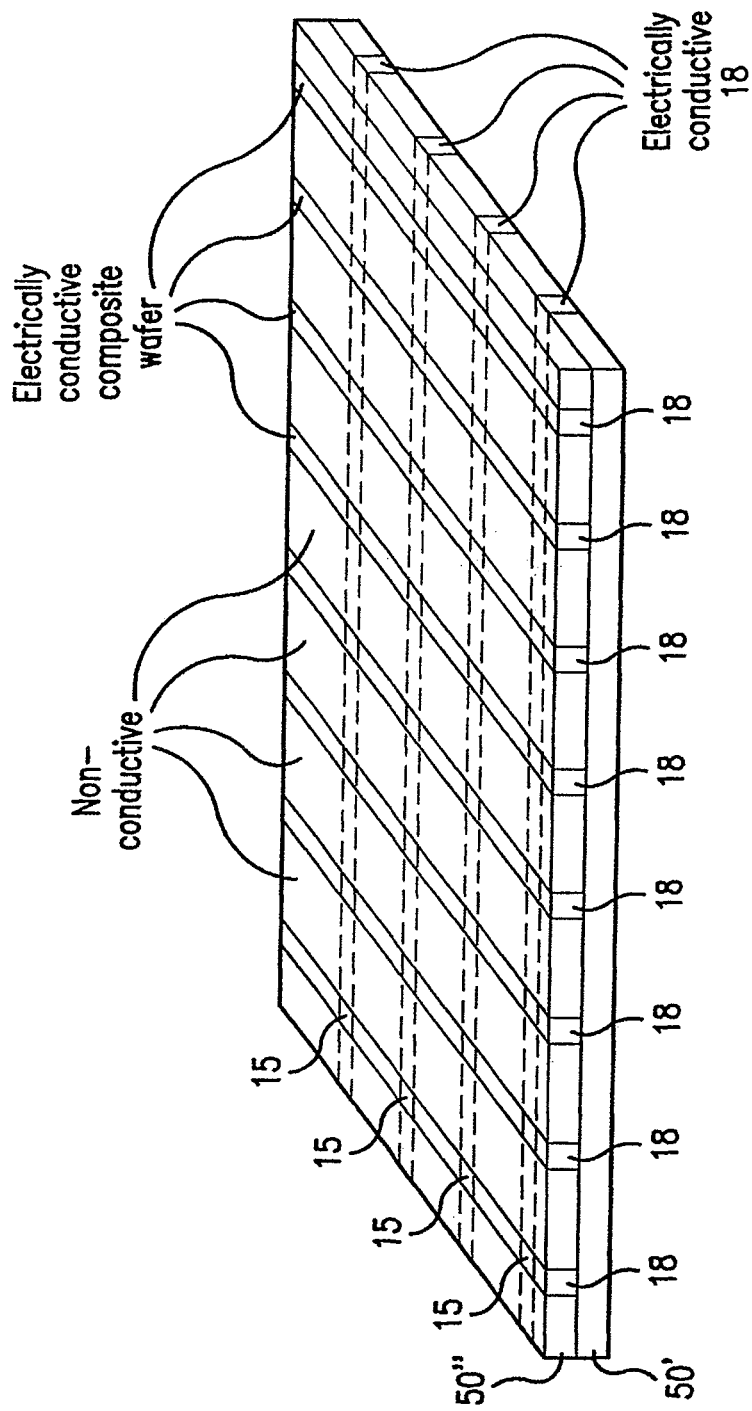
FIG. 4 illustrates another aspect of the sensor disclosed herein for obtaining pressure data of a junction, showing two stacked sensor sheets, each sheet having a plurality of spaced conductive stripes, the stacked sensor sheets being oriented substantially perpendicular to each other such that an array of sensing points is formed by the overlapping portions of the conductive stripes of the stacked sensor sheets.
Figure 15:
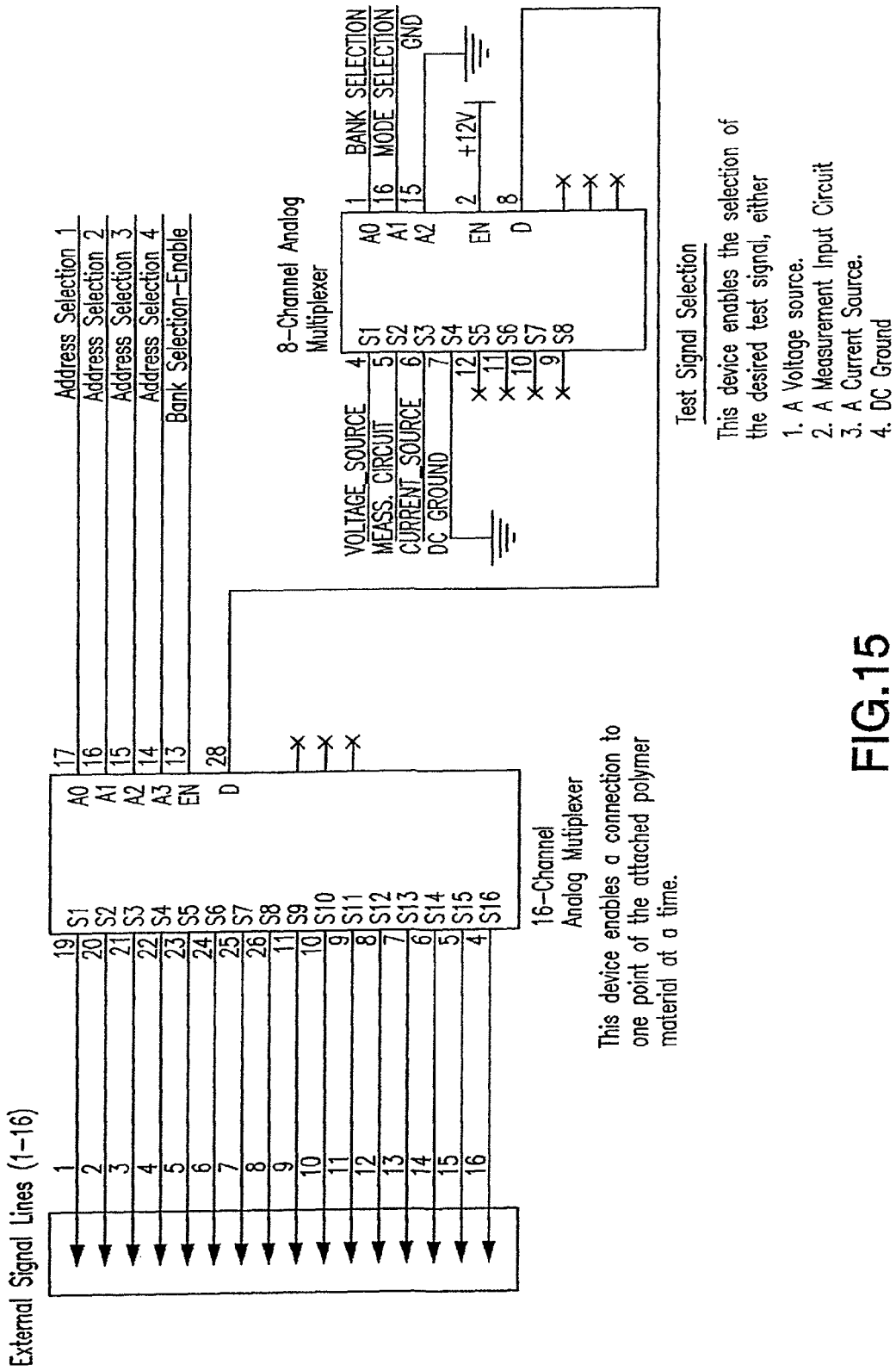
FIG. 15 is a schematic of an exemplary interface circuitry for the data acquisition terminal.

In another aspect, as shown in FIG. 4, the sensors can include multiple stacked polymer sensor sheets. In this aspect, each polymer sensor sheet can have a plurality of conductive stripes of conductive material that are separated by non-conductive polymeric stripes. In the illustrated example, the vertical conductive stripes on one sheet, "columns," and the horizontal conductive stripes on the underlying sheet, "rows," are positioned relative to each other so that, at the places where these columns and rows spatially intersect, the conductive areas of the two sheets are in physical and electrical contact with each other. In one aspect, the exemplary interface electronics illustrated in FIG. 15 can be used with appropriate control software within the data acquisition terminal to connect one column to a voltage source and one row to a current-to-voltage circuit, in order to measure the current through the conductive polymer materials. In one aspect, it is contemplated that each column/row pair, i.e., the internal junction points 15, can be measured, one at a time, to provide a complete set of current measurements. As illustrated, the substantially perpendicular relative orientation of the stacked sensor sheets can allow for formation of an array of sensing points by the overlapping portions of the conductive stripes of the stacked sensor sheets.

Figure 16A:
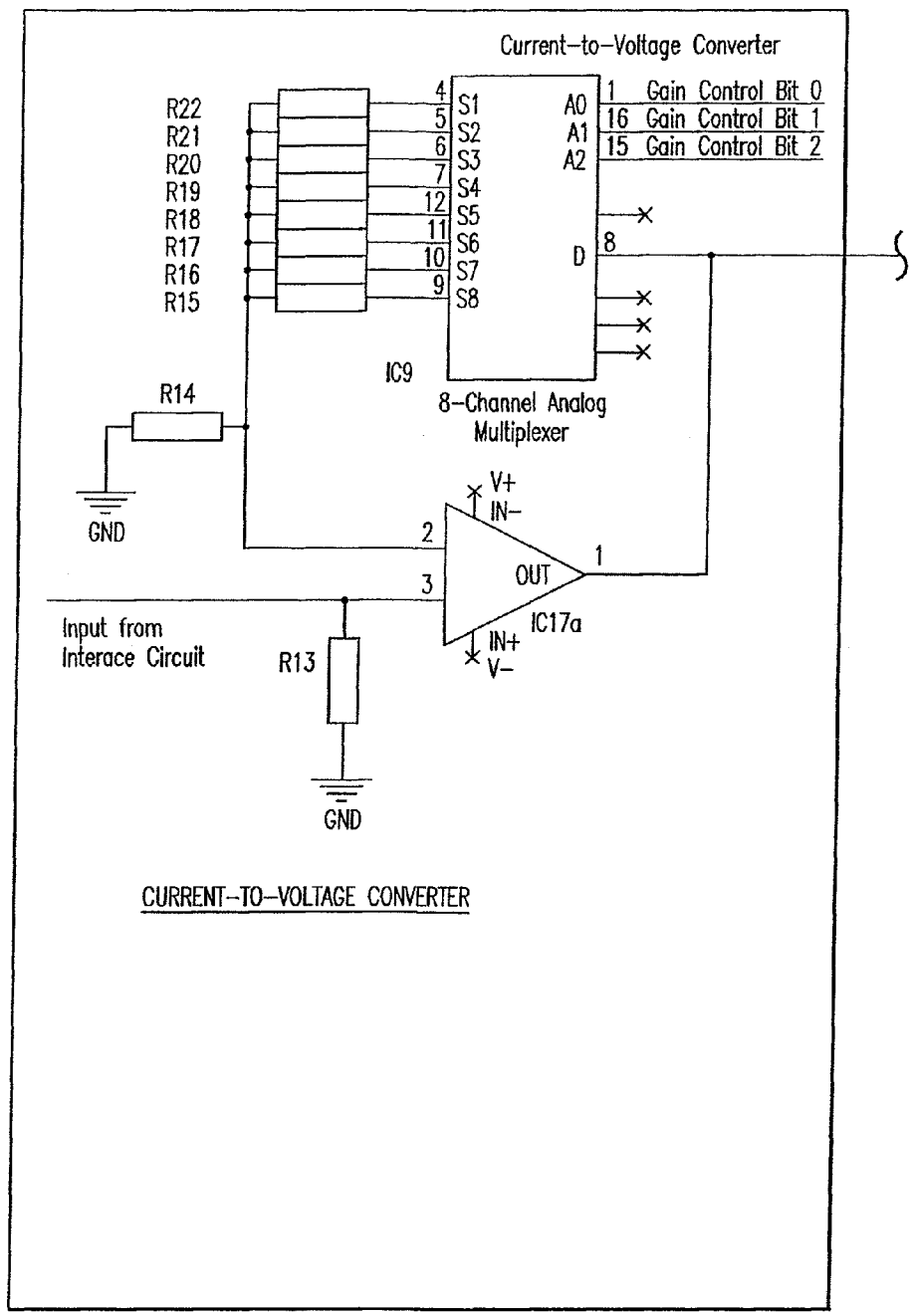
FIGS. 16A-16C are schematics of exemplary measurement circuitry for the data acquisition terminal.
Figure 16B:
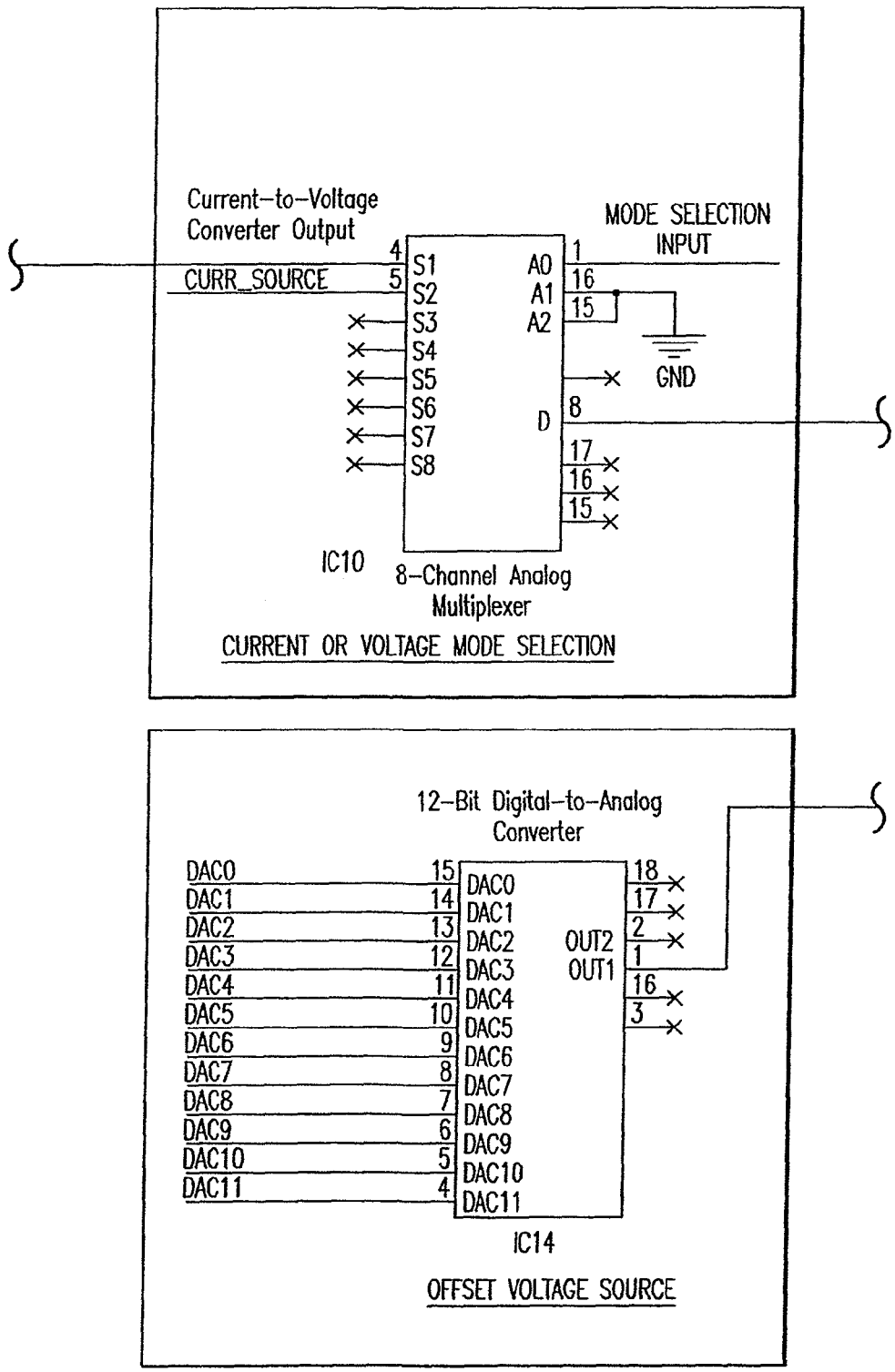
Figure 16C:
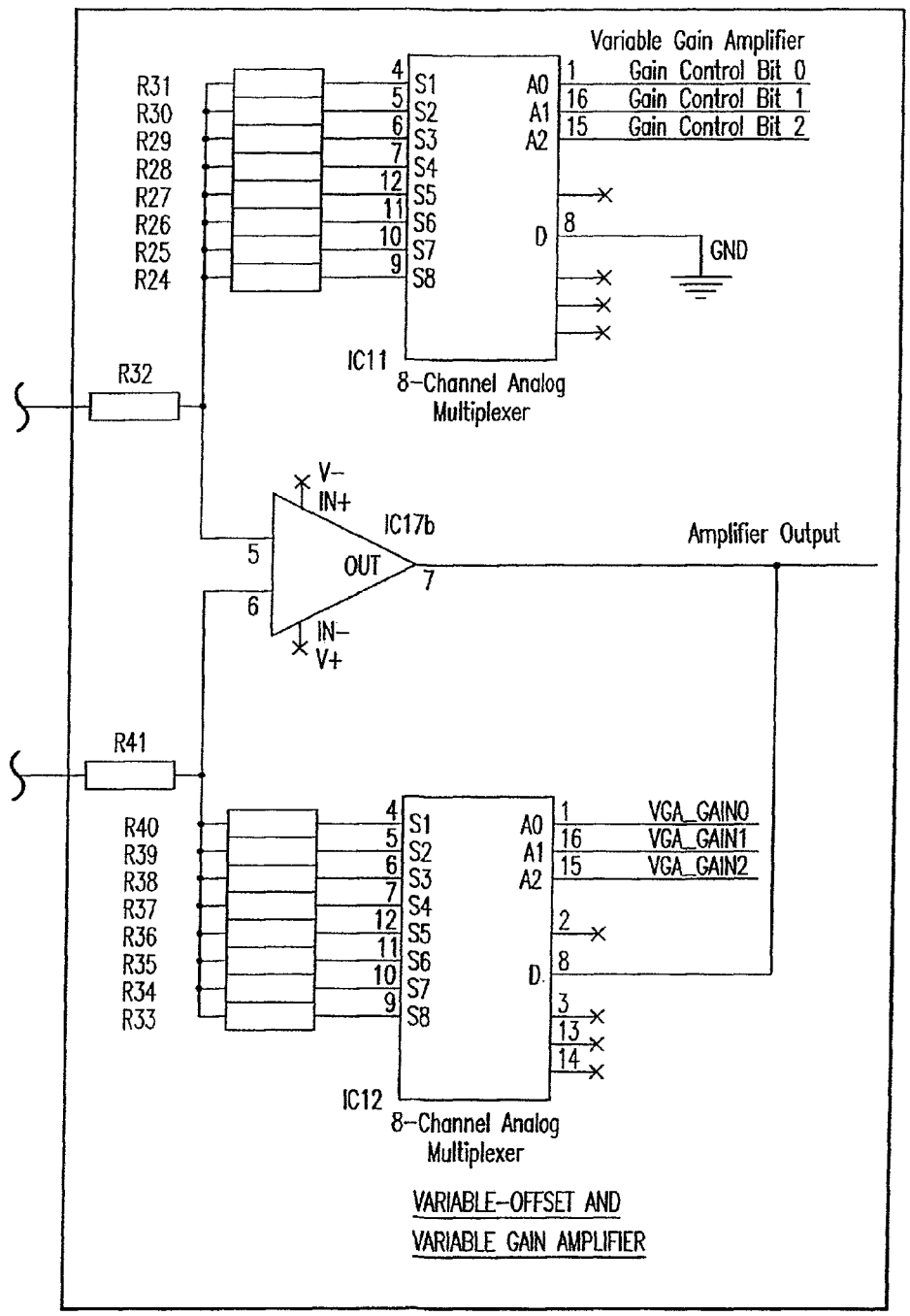

In one aspect, these current measurements do not represent the currents at the pressure-sensitive points in the stacked polymer sheets where the stripes overlap. Rather, the current measurements can be external measurements at external points (also called "nodes"), which are generally near the outer edges of the material. The measurement data are processed in software within the data acquisition terminal in order to calculate the individual currents that are present at each measurement point where the columns and rows overlap, and then this information is used to determine the pressure that is applied at each measurement point. An exemplary, non-limiting, schematic of the measurement circuitry is provided in FIGS. 16A-C herein.

In yet another aspect, both subsurface contact data and surface contact data can be gathered from a single sensor through combination of the above-described aspects.

In one aspect, the sensor may comprise a thermoformable polymer, such as, for example and without limitation, ultra high molecular weight polyethylene (UHMWPE), high density polyethylene (HDPE), polyphenylene sulfide (PPS), low density polyethylene (LDPE), acrylonitrile butadiene styrene (ABS), polyvinyl chloride (PVC), nylon, or polyoxymethylene copolymer (POM). In this aspect, the sensor can be formed into the shape of at least a portion of an artificial joint bearing, such as, for example and without limitation, a portion of an artificial joint, a portion of a prosthetic limb, or other prosthesis. Pressure mapping of portions of a joint bearing can provide data necessary to fit the prosthesis to the user with lower wear. In this aspect, a polymer capable of stretching is advantageous due to the non-uniformity of the shape of the prosthesis.

In an additional aspect, it is contemplated that the contact sensors can have a desired hardness. Specifically, when the sensor comprises PPS, it is contemplated that the desired hardness can be about M93 (R125) on the Rockwell scales and about D 85 on the Shore D scale. For example and without limitation, when the sensor comprises UHMWPE, it is contemplated that the desired hardness can be about D 61 on the Shore D scale. For example and without limitation, when the sensor comprises ABS, it is contemplated that the desired hardness can be about R105 on the Rockwell scale. For example and without limitation, when the sensor comprises nylon, it is contemplated that the desired hardness can be about R120 on the Rockwell scale. For example and without limitation, when the sensor comprises PVC, it is contemplated that the desired hardness can be about R112 on the Rockwell scale. For example and without limitation, when the sensor comprises POM, it is contemplated that the desired hardness can be about R120 on the Rockwell scale.

In another aspect, the sensors can be manufactured in a two stage process. First, the non-conductive sheets of thermoformable polymer can be molded from raw material. Second, the conductive strips can be added to the sensor sheet and placed back into the same mold. In this manner, flow of the non-conductive polymer into the conductive region of the sheet, and flow of the polymer with conductive filler into the non-conductive region of the sheet can be minimized to ensure that, when thermoformed, there is no cross-talk between adjacent conductive strips.

In this aspect, calibration of the each sensor can be performed prior to the thermoforming step, as calibration after thermoforming can prove to be more difficult. It is believed that the characteristics of the sensors do not substantially change during the thermoforming process.

In one aspect, such calibration may be desired as each individual sensor can have individually unique electrical properties that must be calibrated to a standard in order to achieve a desired degree of load measurement accuracy. Further, it is believed that the individual sensors can experience hysteresis when the sensors are unloaded. Thus, it is contemplated that conventional signal processing components configured to correlate the voltage or current to the load of the respective sensor can be implemented using software configured to correlate the load during loading and load during unloading. To compensate for the observed hysteresis effect, it is also contemplated that the software can be configured to calculate the load during a static position—when the load is substantially constant—by using a mean point between a calculated load value during loading and a calculated load value during unloading.

When used in making a prosthetic limb, for example, the sensor sheets can be thermoformed into the shape of a cup for receiving the anatomical limb. Once the sheets are used to map out the force distribution in the cup, the sensor sheets can be adjusted accordingly. This process can be repeated until the forces are substantially uniformly distributed as desired. Once the desired level of force distribution is achieved, a mold, such as for example, a plaster mold, can be made of the interior portion of the cup. Then the mold can be used to form the cup out of materials that are suitable for the prosthesis.

Optionally, the composite materials produced as described herein can be incorporated into one or more sensor sheets. In one aspect, a method for producing the sensor sheets can comprise providing a plurality of substantially circular virgin sheets comprising at least one virgin material. In this aspect, the virgin material can comprise, for example and without limitation, virgin UHMWPE. In another aspect, the method for producing the sensor sheets can comprise providing a plurality of substantially circular composite sheets comprising at least one composite material as disclosed herein. In this aspect, the composite material can comprise, for example and without limitation, a mixture of carbon black and UHMWPE. In an additional aspect, the virgin sheets can have an outer diameter substantially equal to an outer diameter of the composite sheets. In yet an another aspect, the virgin sheets can have an inner diameter substantially equal to an inner diameter of the composite sheets. In a further aspect, the method for producing the sensor sheets can comprise positioning the virgin sheets and the composite sheets can be stacked in a desired configuration. In this aspect, the desired configuration can comprise a single stack of alternating virgin and composite sheets such that virgin sheets are intermediate and in contact with composite sheets and composite sheets are intermediate and in contact with virgin sheets.

In one exemplary aspect, while the virgin and composite sheets are stacked in the desired configuration, the virgin and composite sheets can be subjected to a conventional compression molding process for heating and then fusing the virgin and composite sheets together. In this aspect, the virgin material can comprise UHMWPE. In another aspect, the compression molding of the virgin and composite sheets can produce a substantially cylindrical billet. In this aspect, the substantially cylindrical billet can be substantially hollow. In a further aspect, the billet can be placed on a conventional mandrel. In this aspect, the mandrel can be configured to spin at a desired rate. In still a further aspect, the method for producing the sensor sheets can comprise spinning the mandrel, thereby turning the billet as the mandrel spins. In another aspect, the method can comprise subjecting the billet to a conventional skiving machine. It is contemplated that the skiving machine can comprise a blade for slicing or shaving off a thin layer of the billet. In operation, the blade of the skiving machine advances toward the billet at a constant rate as the billet rotates on the mandrel, thereby producing the sensor sheets. In one aspect, the sensor sheets can be of substantially uniform thickness. In this aspect, it is contemplated that the sensor sheets can have a thickness ranging from about 0.001 inches to about 0.050 inches, more preferably from about 0.002 inches to about 0.030 inches, and most preferably from about 0.003 inches to about 0.020 inches.

In another exemplary aspect, while the virgin and composite sheets are stacked in the desired configuration, the virgin and composite sheets can be subjected to a conventional compression molding process for separately heating and shaping the virgin and composite sheets. In this aspect, the virgin material can comprise PPS. In an additional aspect, the virgin and composite sheets can be joined together using a glue, such as, for example and without limitation, a cyanoacrylate, an epoxy, and the like. As one skilled in the art will appreciate, because PPS and many other conventional polymers have a significantly lower melt viscosity that UHMWPE, compression molding of the composite material with the PPS would lead to undesired mixing of the virgin and composite materials, thereby destroying the existence of discrete conductive and non-conductive portions on the contact surface.

In a further aspect, prior to joining of the virgin and composite materials, it is contemplated that the surfaces of the virgin and composite sheets can be subjected to one or more desired treatments. In this aspect, the one or more desired treatments can comprise, for example and without limitation, flame treatment, chemical etching, chemical preparation, and the like. It is contemplated that after gluing of the virgin and composite materials, the virgin and composite materials can form a single, unified element that can be machined without any risk of the individual pieces of material becoming separated from the unified element. Accordingly, it is further contemplated that the resulting element can be selectively machined without producing any gaps or inconsistencies at the junctions between the virgin and composite materials and between multiple sheets of material.

As one of skill in the art will appreciate, the characteristics of the virgin material used to produce the contact sensor can be analyzed to determine the suitability of the contact sensor for particular applications. For example, PPS can be easily sterilized by autoclave sterilization, whereas UHMWPE lacks the temperature resistance needed for autoclaving. Thus, it is contemplated that PPS can be selected as a virgin material for use in contact sensors that need to be re-useable. However, UHMWPE is significantly cheaper than PPS. Therefore, UHMWPE can be selected as a virgin material for use in contact sensors that will be disposable. Similar characteristics, including mechanical and sensitivity properties, of other conventional engineering polymers can also be examined to determine the adequacy of these polymers for use in the contact sensors disclosed herein. One of the above-discussed methods for producing the contact sensors can be selected for each polymer depending on an analysis of the melt viscosity and other characteristics of the polymer.

In another embodiment, it is contemplated that the sensor 10 can be used intraoperatively during orthopedic implant surgery. The sensor 10 can allow for monitoring of, for example and without limitation, at least one of: the i) force between an orthopedic implant or other medical devices and the patient, ii) force or pressure between a trial joint component and the underlying bone, iii) forces internal to a medical device, iv) force or pressure between a trial component and other orthopedic components, v) forces or pressures of surrounding soft tissue structures on the trial component. For example and without limitation, the sensor 10 described herein can be used in association with: a) the tibial, femoral, or patellar components of a prosthesis used in a total knee replacement procedure; b) the femoral or acetabular components of a prosthesis used in total hip implant procedure; c) the scapular or humeral components of a prosthesis in a shoulder replacement procedure; d) the tibia and talus components of a prosthesis used in an ankle replacement procedure; and e) devices implanted between the vertebral bodies in lumbar or cervical spine disk replacement procedures. As one skilled in the art will appreciate, the intra-operative observation of the forces in the joint allows surgeons to better understand the kinematics of the joint, including the effects of load magnitude and/or load imbalance, thereby enabling the surgeon to make critical adjustments regarding component selection, component position, and the performance of intra-operative soft tissue procedures.

For example, in one aspect, the disclosed sensors 10 can use similar materials as those found in an artificial knee implant. It is of course contemplated that the insert can include any polymeric insert portion of any desired implant. However, in this example and for clarity, the description below will describe the insert as a tibial insert that is conventionally sized for use with a knee implant during a TKA procedure. In this aspect, it is contemplated that the tibial inserts of the knee implant can be formed with at least one discrete sensing points 12. The discrete sensing points can be randomly spaced on the contact surface 8 of the sensor 10. Alternatively, the discrete sensing point(s) can be positioned in a predetermined array on the contact surface. In various optional aspects and without limitation, it is contemplated that the discrete sensing point(s) can comprise at least 20% of the surface area of the contact surface of the insert, at least 30% of the surface area of the contact surface of the insert, at least 40% of the surface area of the contact surface of the insert, at least 50% of the surface area of the contact surface of the insert, at least 60% of the surface area of the contact surface of the insert, at least 70% of the surface area of the contact surface of the insert, at least 80% of the surface area of the contact surface of the insert, or at least 90% of the surface area of the contact surface of the insert.

In one aspect, it is contemplated that the tibial insert can be implanted with the knee implant, which provides for operative sensing during and after the implantation procedure, or, optionally, it is contemplated that the tibial insert can be a trial insert. In this latter instance, the trial tibial insert can be inserted so that the soft tissue balancing can be accomplished with active force/pressure feedback on the joint. After the balancing is complete, an implantable tibial insert, of the same dimensions of the trial tibial insert, can replace the trail tibial insert within the implant. In this aspect, the trial tibial inserts can use the sensing technology described herein to quantify the force being applied to each side of the implant, thereby allowing surgeons to more precisely carry out the important step of soft tissue balancing, which, in turn, reduces the rate of early failure of artificial knee joints.

In a conventional TKA procedure, the surgeon typically removes the worn, exposed bone areas on the femur and/or tibia, reshapes the remaining bones, and replaces these damaged bone areas with new, durable artificial implant devices prosthesis. In the procedure, the femur, tibia, and patella are reshaped and prepared to receive the new knee implant prosthesis using conventional surgical alignment tools.

Subsequently, a femoral implant is then attached to the formed reshaped surface on the femur. Next, a tibial tray implant with a polymeric tibial insert is attached to the formed reshaped surface of the tibia. In addition, a patellar implant is coupled to the reshaped surface of the patella. When positioned within the knee, the femoral implant faces and abuts the polymeric tibial insert positioned therein the tibial tray implant. The femoral implant and the tibial tray implant generally have mounting members that extend outwardly from their respective bottom surface that are configured to extend inwardly into the respective femur and tibia bone, which aid in stabilizing and fixing the femoral and metal tray implants with respect to the reshaped bones. Conventionally, the femoral and tibial tray implants are formed of metal material. As one will appreciate, the polymeric tibial insert separates the femoral implant and the tibial tray implant, which prevents the implants from rubbing together and causing wear spots due to friction. The polymeric tibial insert also absorbs and disperses the pressure imposed by a person's weight.

Generally, after inserting the components, the surgeon tests the knee joint's range of motion intraoperatively by elevating and lowering the knee, bending and extending the leg, and ensuring there are no gaps between the femoral and tibial implants. Testing the joint's range of motion ensures the implants have not been mal-aligned, which, as described above, could lead to adverse post-surgical complications.

Subsequent to testing the implant prosthesis, the' implant components are removed and prepared for permanent insertion. Typically, cement is applied to desired portions of the components, which are then re-inserted and fixed into their permanent positions. The cement is allowed to harden, and range of motion tests are then performed again before the incision is closed and surgery is complete.

In one embodiment, sensor 10, which comprises at least one discrete sensing point 12, can be used in conjunction with an artificial joint implant to provide quantitative data for contact between bones and an implant during orthopedic implant surgery. It is contemplated that the sensor can also indirectly read the pressures, strains, and forces that the soft tissue places on the implant. A surgeon performing a joint replacement procedure can use this data to make necessary adjustments to the implants, bones, and associated tissue while performing the procedure, thereby reducing the risk of post operative complications. In one preferred aspect, the sensor can comprise the polymeric tibial insert.

In one exemplary method of using the sensor 10 to measure joint characteristics during revision joint replacement surgery, the joint is prepared for implant insertion and the joint replacement implant components, such as, for example, the femoral implant and the tibial tray implant and the sensor 10 in the form of the polymeric trial tibial insert, are positioned within the joint. The joint is then articulated through a partial or full range of motion. The force/pressure exerted on the sensor throughout the movement range is sensed and displayed or otherwise conveyed to the surgeon, who may then adjust the size or position of the implants and/or conduct the tissue balancing process based on the sensed pressure data. This sensing/adjustment cycle can be repeated as necessary to achieve a desired balance and alignment within the joint. Once no further adjustments are needed, the surgeon can remove the sensor (i.e., in this example, the trial tibial insert), re-insert a conventional tibial insert, fix the joint replacement implant into position, and close the incision. Optionally, it is contemplated that the joint replacement implant can be fixed into position using the trial tibial insert as the permanent tibial insert.

The contact sensors described herein may be better understood with reference to the Examples set forth below.

EXAMPLE 1

An industrial-grade UHMWPE powder (GUR 1150, available from Ticona Engineering Polymers) having a molecular weight of $6 \times 10^6$, density of 0.93 g/mL, Tm of 135° C., and an average particle size of 100 μm, was combined with carbon black (CB) (Printex L-6 available from Degussa Hulls, Dusseldorf, Germany) having a primary particle size of 18 nm and dibutyl phthalate absorption of 120 mL/100 g. Amounts of each powder were placed in a 120 mL plastic sample container and initially manually shaken for 5 minutes to obtain four different samples having CB weight percentages of 0.25%, 0.5%, 1%, and 8%. The samples were then mixed for 10 minutes on a common laboratory vortex at the maximum speed setting.

Virgin UHMWPE powder and the four UHMWPE/CB powder mixtures were then compression-molded into rectangular sheets 12 cm long, 8.5 cm wide, and 2 mm thick using a mold consisting of a 2 mm thick Teflon frame sandwiched between 2 stainless steel plates that were coated with Teflon mold release spray. The powders were processed in a laboratory press (Carver Laboratory Press, Model C, Fred S. Carver Inc., Wabash, Ind.) equipped with electric heaters for 20 minutes at a temperature of 205° C. and a pressure of 10 MPa. The specimens were then quenched under pressure at a cooling rate of 50° C./min.

Figure 6:
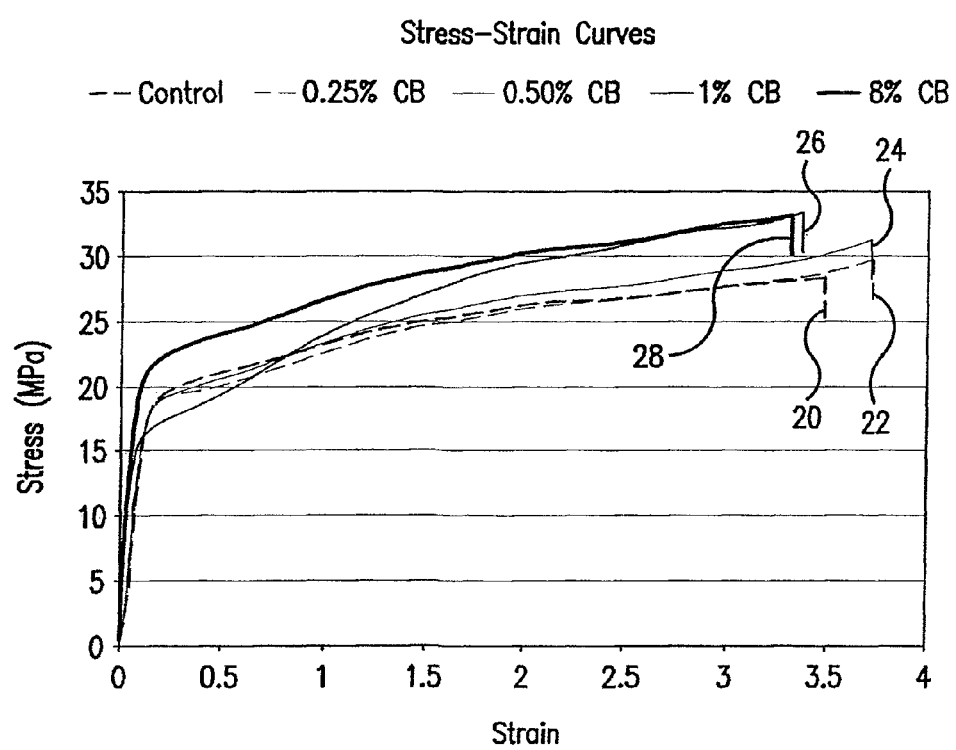
FIG. 6 graphically illustrates the stress v. strain curve for exemplary composite conductive materials as described herein.

Tensile tests were performed to obtain stress-strain curves for each composite and for the control. Results can be seen in FIG. 6 for the control (20), 0.25% CB (22), 0.50% CB (24), 1.0% CB (26), and 8.0% CB (28). From these stress-strain curves, the modulus of elasticity was determined for each composite, and these values were compared to those obtained for the control specimen. Both the control specimens and the composite specimens were formed from the same stock of virgin UHMWPE powder (GUR 1150) by using the same processing parameters of temperature, pressure, time, and cooling rate. The results from the tensile tests can be seen in Table 1, below. It was determined that there was no statistically significant difference ($p=0.32$, $\alpha=0.05$) between the modulus of the 8% composite and the modulus of the virgin UHMWPE control samples that were tested.

| n = 4 | Control | 0.25 wt % CB | 0.50 wt % CB | 1 wt % CB | 8 wt % CB |
| --- | --- | --- | --- | --- | --- |
| Young's Modulus (MPa) | 214.8 ± 21.1 | 208.48 ± 7.68 | 211.9 ± 7.74 | 212.6 ± 6.82 | 208.9 ± 11.1 |
| Tensile Strength (MPa) | 30.8 ± 3.98 | 29.1 ± 2.23 | 32.6 ± 3.49 | 31.9 ± 2.43 | 31.7 ± 1.03 |
| Yield Strength (MPa) | 17.8 ± 0.75 | 18.0 ± 0.87 | 17.8 ± 0.93 | 15.2 ± 0.96 | 22.2 ± 1.07 |
| Elongation at Break (%) | 390 ± 77.0 | 360 ± 18.0 | 390 ± 18.0 | 340 ± 23.0 | 290 ± 41.0 |

The elastic modulus values obtained were comparable to those obtained by Parasnis and colleagues for thin-film UHMWPE specimens (see Parasnis C, Ramani K. Analysis of the effect of pressure on compression molding of UHMWPE. Journal of Materials Science Materials in Medicine, Vol. 9, p 165-172, 1998, which is incorporated herein by reference). The values obtained for tensile strength, yield strength, and elongation at break compared closely to the values cited in the literature (for example, see is Li S. Burstein A. H., Current Concepts Review: Ultra-high molecular weight polyethylene. The Journal of Bone and Joint Surgery, Vol. 76-A, No. 7, p 1080-1090, 1994, which is incorporated herein by reference).

Figure 7:
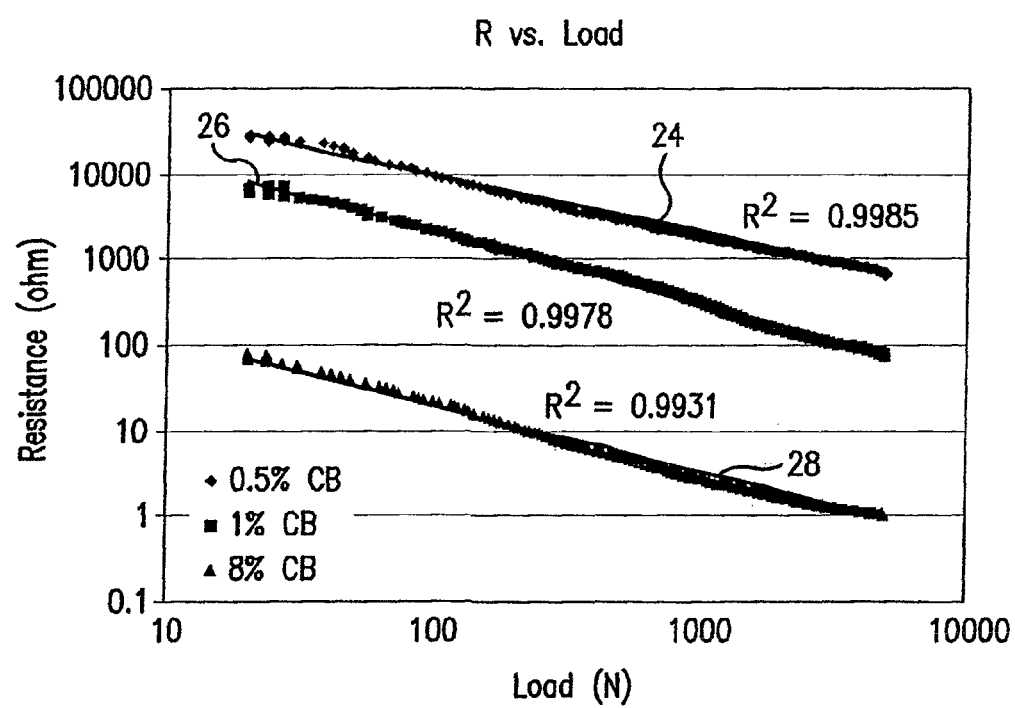
FIG. 7 graphically illustrates the log of resistance vs. log of the load for three different composite conductive materials as described herein.
Figure 8:
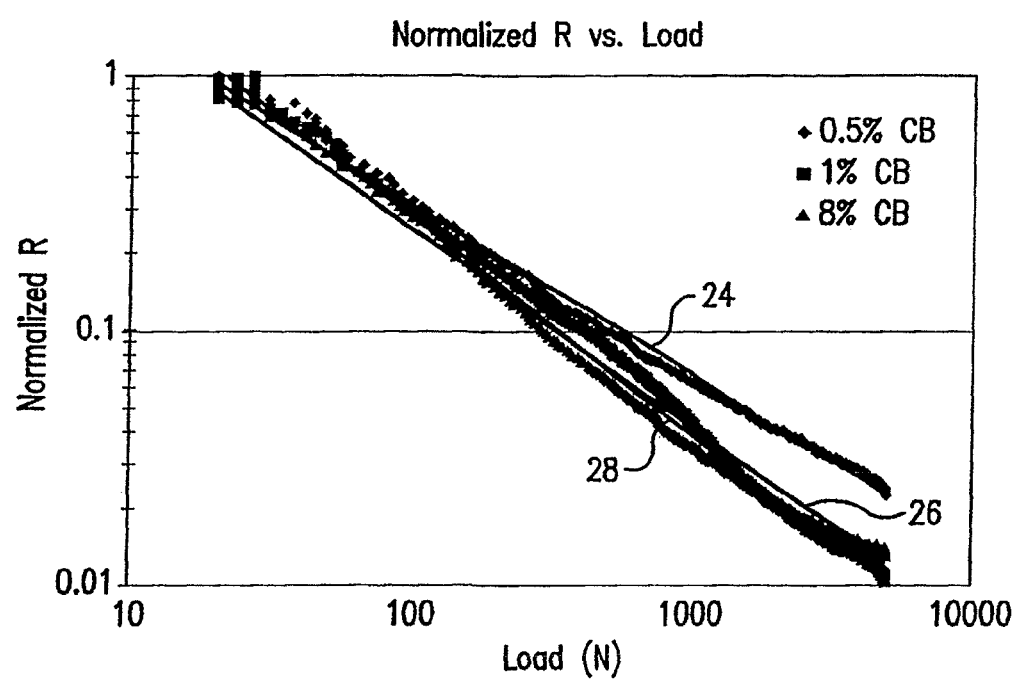
FIG. 8 illustrates the log of normalized resistance vs. log of the load for three different composite conductive materials as described herein.

FIG. 7 shows a plot of the log of the resistance as a function of the log of the compressive load applied to the UHMWPE/CB composites of 0.5% (24), 1% (26), and 8% (28). The plot shows that the composites have the same slope, but that the intercepts are different, with the 0.5% composite having the highest intercept, and the 8% composite having the lowest intercept. The value of resistance changed by about two orders of magnitude for each composite. The correlation coefficients of each regression line indicated a good fit. When the values of resistance were normalized (shown in FIG. 8), the curves for the three composites were very similar, suggesting that the amount of CB only affected the magnitude of the resistance. Thus, the relative response to applied load appeared to be independent of the amount of CB. It should be noted that the control sample and the 0.25% CB sample had high resistance for all loads tested and thus were not included on FIGS. 7 and 8.

Figure 9:
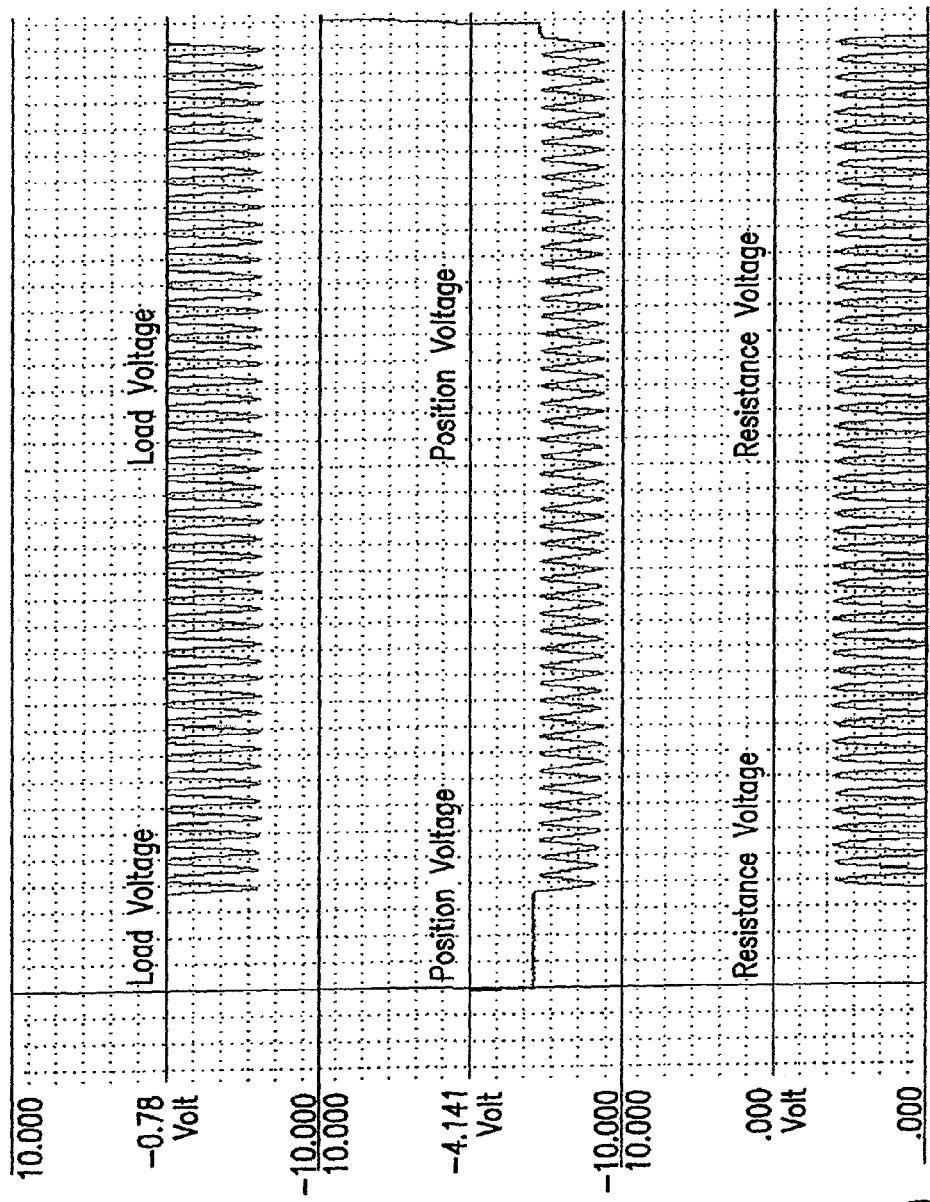
FIG. 9 illustrates the voltage values corresponding to load, position, and resistance of an exemplary composite material.
Figure 10A:
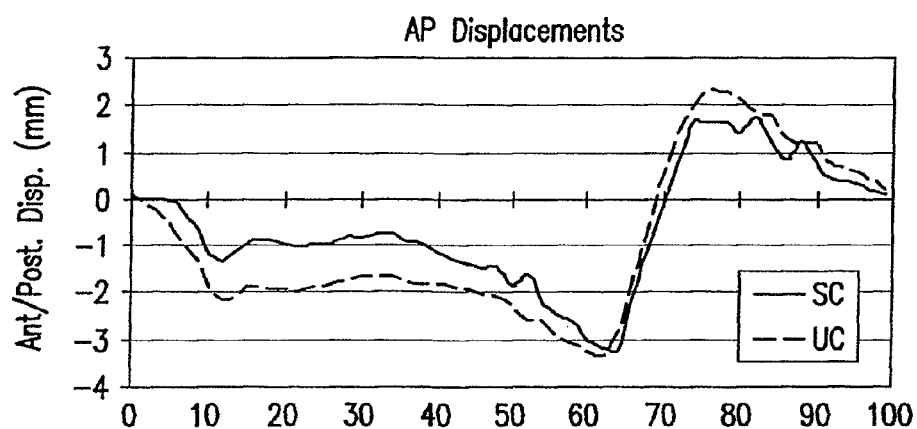
FIGS. 10A-10D illustrate the kinematics and contact area for exemplary artificial knee implant sensors as described herein with different surface geometries.
Figure 10B:
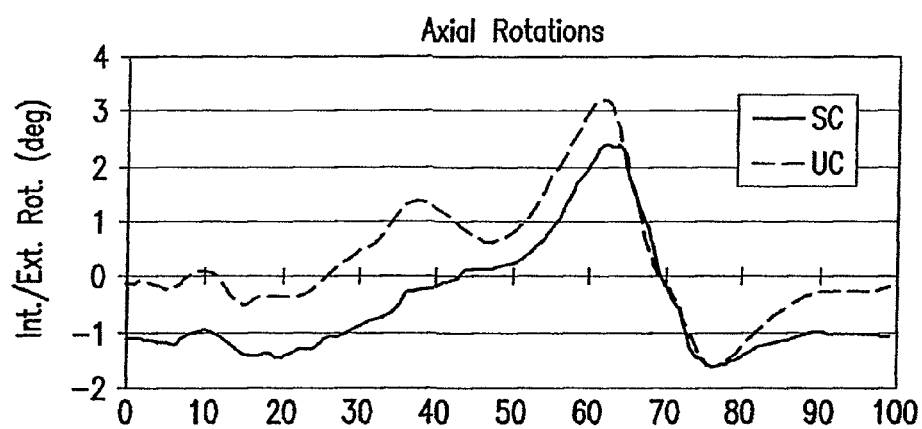
Figure 10C:
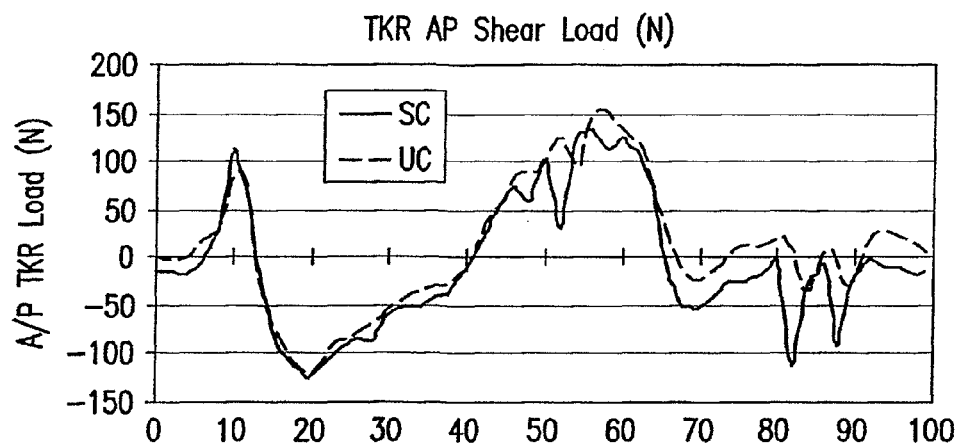
Figure 10D:
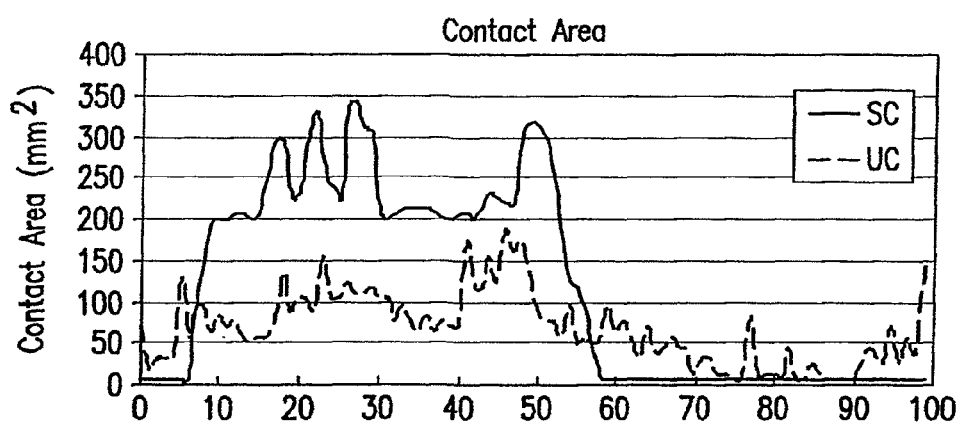

FIG. 9 shows the voltage values corresponding to the compressive load, the compressive displacement, and the resistance of the 8 wt % CB composite while the composite was loaded cyclically with a haversine wave at 1 Hz. The top curve corresponds to the compressive stress, the middle curve corresponds to the compressive strain, and the bottom curve corresponds to the resistance of the sensor material. This data represents the cyclic response of the material, indicating that it does not experience stress-relaxation at a loading frequency of 1 Hz. The results of this cyclic testing show that the peak voltage values corresponding to resistance remain nearly constant over many cycles. Therefore, the data seem to indicate that the sensor material should be well suited for cyclic measurements since the readings do not degrade over time.

Monitoring the electrical resistance of the composite material while applying a compressive load revealed the force-dependent nature of the electrical properties of the material. Because of the nano-scale dispersion of the conductive filler, the material's electrical response to applied load was nearly ideal for all of the percentages tested. That is, the log of the material's resistance varied linearly with respect to the log of the applied load. This linear relationship makes the material well suited for use as a sensor.

The data show that the linear relationship holds true for 0.5%, 1%, and 8%, with the difference between the three being the value of the resistance. As all three percentages showed good sensor properties, specific formulations could be developed based on other criteria, such as the specifics of the measurement electronics.

EXAMPLE 2

Compression molding was used to form 2 rectangular blocks of 1150 UHMWPE doped with 8 wt % carbon black filler as described above for Example 1. The blocks formed included a 28×18 matrix of surface sensing points 12 as shown in FIG. 1. The points were circular with a $\frac{1}{16}^{th}$ inch (1.59 mm) diameter and spaced every $\frac{1}{10}^{th}$ inch (2.54 mm). The blocks were then machined to form both a highly-conforming, PCL-sacrificing tibial insert (Natural Knee II, Ultra-congruent size 3, Centerpulse Orthopedics, Austin, Tex.) and a less conforming PCL-retaining tibial insert (Natural Knee II, Standard-congruent, size 3, Centerpulse Orthopedics, Austin, Tex.) as illustrated in FIG. 1. The implants were then aligned and potted directly in PMMA in the tibial fixture of a multi-axis, force-controlled knee joint simulator (Stanmore/Instron, Model KC Knee Simulator). Static testing was performed with an axial load of 2.9 kN (4.times.B.W.) at flexion angles of 0°, 30°, 60°, and 80°, to eliminate the effects of lubricant and to compare the sensor reading to the literature. The dynamic contact area was then measured during a standard walking cycle using the proposed 1999 ISO force-control testing standard, #14243. Data was collected and averaged over 8 cycles. A pure hydrocarbon, light olive oil was used as the lubricant due to its inert electrical properties.

Static loading of the sensors showed that the contact area of the ultra congruent insert was significantly higher than that of the standard congruent insert at all angles of flexion tested. The data closely agreed with results found in the literature from FEA analysis.

Figure 12:
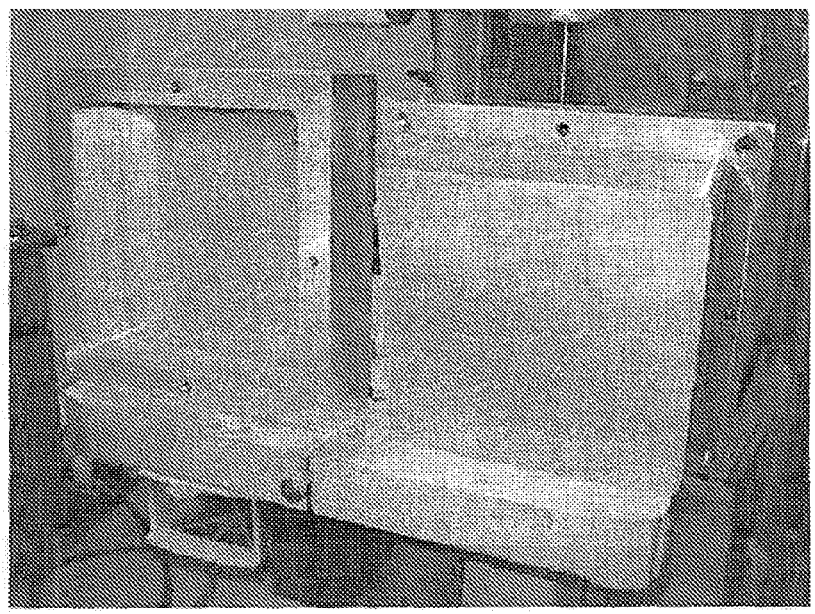
FIG. 12 is a photograph of one aspect of an exemplary mold and press used to form sensor sheets as disclosed herein.

The results from dynamic testing with a standard walking protocol, shown in FIG. 12, show the effects that the lubricant had on the dynamic contact area. Contact area was registered by the sensor when physical contact occurred between the femoral component and any sensing point, allowing electrical current to flow. Because the lubricant was electrically insulating, fluid-film lubrication over a sensing point caused no contact to be registered at that point. The lower contact area measured for the ultra-congruent insert during the stance phase of gait was due to the fluid-film lubrication that occurred with the more conforming insert. The rapid changes in contact area measured for the standard-congruent insert during the mid-stance phase suggests that the mode of lubrication is quite sensitive to the dynamic loading patterns.

EXAMPLE 3

Figure 11A:
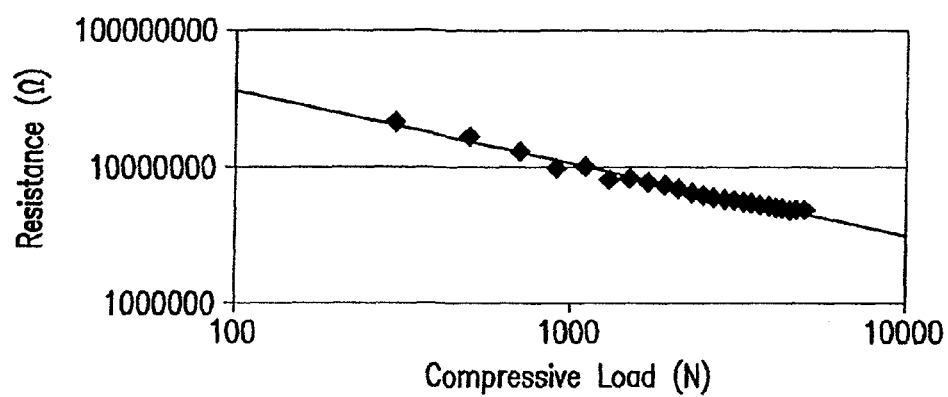
FIGS. 11A and 11B graphically illustrate the log of normalized resistance vs. log of the compressive force for two different composite conductive materials as described herein.
Figure 11B:
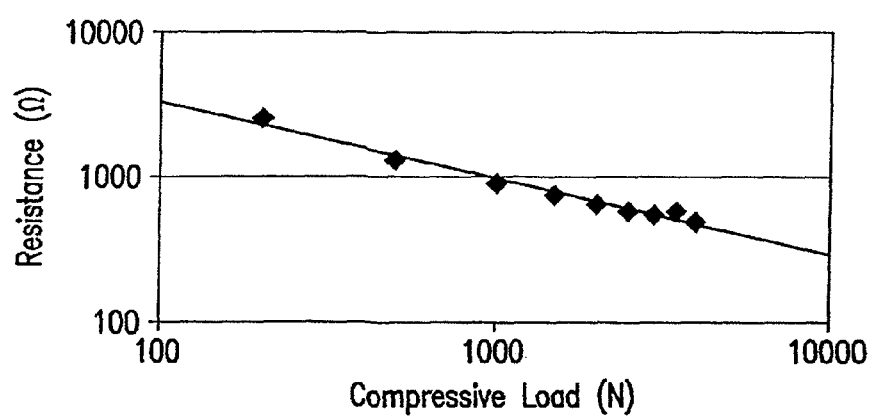

Tecoflex SG-80A, a medical grade soft polyurethane available from Thermedics Inc. (Woburn, Mass.), was solution processed and molded including 4 wt % and 48 wt % CB to form two solid sample materials. FIGS. 11A and 11B graphically illustrate the resistance vs. compressive force applied to the samples for the 4% and 48% non-surfactant mixed samples, respectively. As can be seen, both samples showed pressure sensitive conductive characteristics suitable for forming the sensors as described herein where the value of resistance can be controlled with the amount of conductive filler added.

EXAMPLE 4

A 6"×6" mold was constructed from normalized, pre-hardened 4140 steel with a Rockwell hardness of HRC 32-35. The mold was designed and built to mold 6×6 inch sensor sheets at approximately $\frac{1}{8}^{th}$ inch thick, and is shown in FIG. 12.

The mold was used to form "virgin" non-conductive sheets from raw high density polyethylene (HDPE) in powder form, similar to the fashion to form the sheets of UHMWPE in Example 1. HDPE works well in applications in which the sensor sheets need to be thermoformed. However, HDPE's low gel viscosity makes it a challenge to keep adjacent regions of the sensor sheet separated from one another when forming the sensor sheet.

Although HDPE's melt temperature is readily available, observations were made to confirm how the sensor sheets would behave in the mold. A thermocouple was used to measure the temperature in the oven. It was determined that the transition temperature of the HDPE was 255° Fahrenheit. The mold was heated by upper and lower platens, which also apply compressive force. It was noted that, even with the correct temperature being applied, some smearing could occur in the sensor sheet if compressive forces were not applied evenly. Any flow of the gel caused smearing.

Once the virgin sheets were constructed, the conductive regions were added and the sheets were placed back into the same mold. Since neither the mold nor the press were perfectly square, the sheets that were produced varied by 10-20 thousands of an inch. To minimize these variances, the mold sections and the press sections were labeled on each corner. Once the mold was labeled, different mold and press alignments were tested to determine the alignments the produced the sheets with the least variance.

Raw material in powder form was melted in the mold under the optimal alignment determined previously to produce the virgin sensor sheet. The conductive filler portions were placed on the virgin sensor sheet. Then, the sheet with the conductive filler was placed back into the mold with the same alignment to ensure that any dimensional variance that were present during the initial molding will also be present for the second molding. It was found that this procedure reduced material flow inside the mold during gel state, which reduced smearing.

These and other modifications and variations to the present invention may be practiced by those of ordinary skill in the art, without departing from the spirit and scope of the present invention, which is more particularly set forth in the appended claims. In addition, it should be understood that aspects of the various aspects may be interchanged either in whole or in part. Furthermore, those of ordinary skill in the art will appreciate that the foregoing description is by way of example only, and is not intended to limit the invention so further described in such appended claims.

We claim:

1. A contact sensor, comprising:
    a data acquisition terminal; and
    a contact surface configured to receive a load applied by an electrically conductive joint element, the contact surface having selected spaced conductive portions, wherein the contact surface extends to a depth of at least about 50 nm,
    wherein the selected spaced conductive portions define an array of sensing points, and wherein the array of sensing points is in communication with the data acquisition terminal, wherein, during application of the load, at least one sensing point of the array of sensing points is configured to produce an output signal indicative of the change in electrical resistance experienced across the contact surface at the sensing point, and wherein the output signal produced by each sensing point corresponds to variations in the load between the electrically conductive joint element and the contact surface.

2. The contact sensor of claim 1, wherein the conductive portions of the contact surface form conductive stripes extending the substantial length of the contact surface.

3. The contact sensor of claim 1, wherein the conductive portions of the contact surface form a plurality of dots spaced along the contact surface.

4. The contact sensor of claim 1, wherein the data acquisition terminal is programmed to measure the current at each sensing point of the array of sensing points.

5. The contact sensor of claim 1, wherein the data acquisition terminal is programmed to process the current measurements at least one sensing point to determine the pressure that is applied at each sensing point.

6. The contact sensor of claim 1, wherein the conductive portions of the contact surface are formed from a pressure sensitive conductive composite material that comprises an electrically conducive filler and a polymeric material.

7. The contact sensor of claim 6, wherein the non-conductive portion of the sensor is formed from a polymeric material.

8. The contact sensor of claim 7, wherein the polymeric material used in the conductive and non-conductive portions of the sensor are the same polymeric material.

9. The contact sensor of claim 1, wherein the polymeric material is a thermoformable polymer.

10. The contact sensor of claim 1, wherein the polymeric material is selected from a group consisting of: ultra high molecular weight polyethylene (UHMWPE), high density polyethylene (HDPE), polyphenylene sulfide (PPS), low density polyethylene (LDPE), or polyoxymethylene copolymer (POM).

11. The contact sensor of claim 10, wherein a desired amount of conductive filler can range from about 0.1% to about 20% by weight of the pressure sensitive composite material.

12. The contact sensor of claim 10, wherein a desired amount of conductive filler can range from about 1% to about 15% by weight of the pressure sensitive composite material.

13. The contact sensor of claim 10, wherein a desired amount of conductive filler can range from about 5% to about 12% by weight of the pressure sensitive composite material.

14. The contact sensor of claim 10, wherein the conductive filler comprises carbon black.

15. The contact sensor of claim 1, wherein the pressure sensitive composite material further comprises ceramic fillers, aluminum oxide, zirconia, calcium, silicon, fibrous fillers, carbon fibers, glass fibers, and/or organic fillers.

16. The contact sensor of claim 1, wherein the contact sensor can be formed into the shape of at least a portion of an artificial joint bearing.

17. The contact sensor of claim 1, wherein the contact surface extends to a depth of less than about 1000 nm.

18. A contact sensor, comprising:
    a data acquisition terminal; and
    a surgical insert defining a contact surface configured to receive a load applied by an electrically conductive joint element, the contact surface having selected spaced conductive portions, wherein the selected spaced conductive portions define an array of sensing points, wherein the array of sensing points is in communication with the data acquisition terminal, wherein the contact surface extends to a depth of at least about 50 nm, and wherein the surgical insert is configured for insertion therein a selected joint within the body of a subject, wherein, during application of the load, at least one sensing point of the array of sensing points is configured to produce an output signal indicative of the change in electrical resistance experienced across the contact surface at the sensing point, and wherein the output signal produced by each sensing point corresponds to variations in the load between the electrically conductive joint element and the contact surface.

19. The contact sensor of claim 18, wherein the selected joint comprises one of a knee joint, a hip joint, a shoulder joint, an ankle joint, and a spinal joint, 20. The contact sensor of claim 19, wherein the surgical insert comprises one of a tibial insert, a femoral insert, a patellar insert, an acetabular insert, a scapular insert, a humeral insert, a talar insert, and a vertebral insert.

21. The contact sensor of claim 18, wherein the contact surface extends to a depth of less than about 1000 nm.

* * * * *